US007245985B2

(12) United States Patent
Magill et al.

(10) Patent No.: US 7,245,985 B2
(45) Date of Patent: Jul. 17, 2007

(54) PROCESS AND APPARATUS FOR IMPROVING AND CONTROLLING THE VULCANIZATION OF NATURAL AND SYNTHETIC RUBBER COMPOUNDS

(75) Inventors: Richard Magill, Cheyenne, WY (US); John C. Van Doren, Bailey, CO (US); Bruce Sellers, Fort Collins, CO (US); Tim Erickson, Parker, CO (US); Scott Schneider, Littleton, CO (US); Steve Courington, Lone Tree, CO (US); Lance Bethel, Westminster, CO (US)

(73) Assignee: Signature Control Systems, Denver, CO (US)

( * ) Notice: Subject to any disclaimer, the term of this patent is extended or adjusted under 35 U.S.C. 154(b) by 327 days.

(21) Appl. No.: 10/800,079

(22) Filed: Mar. 11, 2004

(65) Prior Publication Data

US 2005/0119785 A1    Jun. 2, 2005

Related U.S. Application Data

(63) Continuation-in-part of application No. 10/666,433, filed on Sep. 18, 2003, now abandoned, which is a continuation-in-part of application No. 10/267,197, filed on Oct. 8, 2002, now Pat. No. 6,855,791, and a continuation-in-part of application No. 10/102,614, filed on Mar. 19, 2002, now Pat. No. 6,774,643, and a continuation-in-part of application No. 09/815,342, filed on Mar. 21, 2001, now abandoned.

(60) Provisional application No. 60/394,736, filed on Jul. 9, 2002, provisional application No. 60/278,034, filed on Mar. 21, 2001.

(51) Int. Cl.
*B29C 39/00* (2006.01)
*G06F 19/00* (2006.01)
*G06G 7/66* (2006.01)
*G01R 27/00* (2006.01)

(52) U.S. Cl. .................. 700/198; 700/109; 700/199; 700/204; 700/205; 702/65; 702/84; 702/179; 264/40.1

(58) Field of Classification Search ............... 700/2, 700/9, 11, 12, 19, 28, 32, 44, 51, 95, 108–110, 700/197–205; 702/65, 81–83, 176, 179; 264/40.1

See application file for complete search history.

(56) References Cited

U.S. PATENT DOCUMENTS 2,765,219 A    10/1956    Shawhan ............... 23/253

(Continued)

FOREIGN PATENT DOCUMENTS

EP    0 313 435    4/1989

(Continued)

OTHER PUBLICATIONS

U.S. Appl. No. 10/102,614, filed Mar. 19, 2002, Magill.

(Continued)

*Primary Examiner*—Leo Picard
*Assistant Examiner*—Sean Shechtman
(74) *Attorney, Agent, or Firm*—Sheridan Ross P.C.

(57) ABSTRACT

A process for curing a natural or synthetic rubber compound under a plurality of curing conditions by: (1) obtaining time dependent data streams of dielectric or impedance values from a non-bridged impedance sensing circuit and a capacitor having the rubber compound being cured as a dialectric; (2) determining impedance related measurements from the obtained data streams; (3) determining a predictive curing equation by performing a multiple regression between: (a) reheometric data obtained from a plurality of different rubber compound samples cured in a rheometer at various environmental curing conditions, and (b) corresponding samples cured in a production mold at the same environmental conditions; (4) adjusting the curing equation to obtain cured parts having one or more desired properties; and (5) controlling the mass producing cured parts with a controller that uses the curing equation for predicting a cure time for each part, wherein the predictions are effective over variations in the rubber compound, and in the mold temperature.

31 Claims, 20 Drawing Sheets

U.S. PATENT DOCUMENTS

| | | | |
|---|---|---|---|
| 3,600,676 A | 8/1971 | Lugwig et al. | |
| 3,746,975 A | 7/1973 | Malthy | 324/65 R |
| 3,753,092 A | 8/1973 | Ludlow et al. | 324/61 R |
| 3,778,705 A | 12/1973 | Malthy | 324/61 R |
| 3,781,672 A | 12/1973 | Malthy et al. | 324/61 R |
| 3,807,055 A | 4/1974 | Kraxberger | |
| 3,879,644 A | 4/1975 | Malthy | 317/246 |
| 3,985,712 A | 10/1976 | Garst | 260/75 M |
| 4,107,599 A | 8/1978 | Preikschat | |
| 4,261,525 A | 4/1981 | Wagner | |
| 4,331,516 A | 5/1982 | Meighan | 204/2.1 |
| 4,338,163 A | 7/1982 | Rittenhouse | 204/2.1 |
| 4,344,142 A | 8/1982 | Diehr, II et al. | 364/473 |
| 4,373,092 A | 2/1983 | Zsolnay | 528/481 |
| 4,381,250 A | 4/1983 | Rittenhouse | 252/182.1 |
| 4,389,578 A | 6/1983 | Wagner | |
| 4,399,100 A | 8/1983 | Zsolnay et al. | 422/62 |
| 4,423,371 A | 12/1983 | Senturia et al. | 324/61 R |
| 4,433,286 A | 2/1984 | Capots et al. | 324/61 R |
| 4,448,943 A | 5/1984 | Golba et al. | 526/59 |
| 4,496,697 A | 1/1985 | Zsolnay et al. | 526/60 |
| 4,510,103 A | 4/1985 | Yamaguchi et al. | 264/40.2 |
| 4,510,436 A | 4/1985 | Raymond | 324/61 P |
| 4,515,545 A | 5/1985 | Hinrichs et al. | 425/143 |
| 4,546,438 A * | 10/1985 | Prewitt et al. | 700/198 |
| 4,551,103 A | 11/1985 | Vitale | 434/225 |
| 4,551,807 A | 11/1985 | Hsich et al. | 364/473 |
| 4,580,233 A | 4/1986 | Parker et al. | |
| 4,588,943 A | 5/1986 | Hirth | |
| 4,676,101 A | 6/1987 | Baughman | 73/304 C |
| 4,683,418 A | 7/1987 | Wagner et al. | |
| 4,710,550 A | 12/1987 | Kranbuehl | |
| 4,723,908 A | 2/1988 | Kranbuehl | 432/37 |
| 4,773,021 A | 9/1988 | Harris et al. | 364/476 |
| 4,777,431 A | 10/1988 | Day et al. | 324/61 P |
| 4,868,769 A | 9/1989 | Persson | 364/550 |
| 4,881,025 A | 11/1989 | Gregory | 324/61 R |
| 4,896,098 A | 1/1990 | Haritonidis et al. | |
| 5,008,307 A | 4/1991 | Inomata | 523/220 |
| 5,032,525 A | 7/1991 | Lee et al. | 436/55 |
| 5,184,077 A | 2/1993 | Day et al. | 324/693 |
| 5,201,956 A | 4/1993 | Humphrey et al. | 118/716 |
| 5,207,956 A | 5/1993 | Kline et al. | 264/40.6 |
| 5,208,544 A | 5/1993 | McBrearty et al. | 324/687 |
| 5,210,499 A | 5/1993 | Walsh | |
| 5,219,498 A | 6/1993 | Keller et al. | 264/40.2 |
| 5,223,796 A | 6/1993 | Waldman et al. | 324/687 |
| 5,283,731 A | 2/1994 | Lalonde et al. | 364/401 |
| 5,317,252 A | 5/1994 | Kranbuehl | 324/71.7 |
| 5,432,435 A * | 7/1995 | Strong et al. | 324/71.1 |
| 5,453,689 A | 9/1995 | Goldfine et al. | 324/239 |
| 5,459,406 A | 10/1995 | Louge | 324/688 |
| 5,486,319 A | 1/1996 | Stone et al. | 264/406 |
| 5,521,515 A | 5/1996 | Campbell | 324/674 |
| 5,528,155 A | 6/1996 | King et al. | 324/713 |
| 5,569,591 A | 10/1996 | Kell et al. | 435/29 |
| 5,654,643 A | 8/1997 | Bechtel et al. | |
| 5,749,986 A | 5/1998 | Wyatt | 156/64 |
| 5,872,447 A | 2/1999 | Hager, III | 324/71.1 |
| 5,874,832 A | 2/1999 | Gabelich | 324/688 |
| 5,898,309 A | 4/1999 | Becker et al. | 324/689 |
| 5,961,913 A | 10/1999 | Haase | 264/326 |
| 5,996,006 A | 11/1999 | Speicher | 709/218 |
| 6,043,308 A | 3/2000 | Tanahashi et al. | 524/495 |
| 6,114,863 A | 9/2000 | Krahn et al. | |
| 6,124,584 A | 9/2000 | Blaker et al. | |
| 6,281,801 B1 | 8/2001 | Cherry et al. | |
| 6,323,659 B1 | 11/2001 | Krahn | |
| 6,472,885 B1 | 10/2002 | Green et al. | 324/638 |
| 6,490,501 B1 | 12/2002 | Sanders | |
| 6,703,847 B2 | 3/2004 | Venter et al. | |
| 6,708,555 B1 | 3/2004 | Lyons, Jr. et al. | |
| 6,774,643 B2 | 8/2004 | Magill | |
| 6,784,671 B2 | 8/2004 | Steele et al. | |
| 6,784,672 B2 | 8/2004 | Steele et al. | |
| 6,797,660 B2 | 9/2004 | Komatsu | |
| 6,855,791 B2 | 2/2005 | Van Doren et al. | |
| 6,989,678 B2 | 1/2006 | Venter et al. | |
| 7,068,050 B2 | 6/2006 | Steele et al. | |
| 7,068,051 B2 | 6/2006 | Anderson | |
| 7,146,747 B2 | 12/2006 | Studd et al. | |
| 2004/0133301 A1 | 7/2004 | Van Doren et al. | |

FOREIGN PATENT DOCUMENTS

| | | |
|---|---|---|
| EP | 0 540 103 B1 | 2/1996 |
| EP | 0 743 153 A1 | 11/1996 |
| EP | 1 050 888 A1 | 11/2000 |
| EP | 0815458 | 10/2003 |
| FR | 2 645 275 | 10/1990 |
| WO | 9534945 | 12/1995 |
| WO | 9628741 | 9/1996 |
| WO | 9704299 | 2/1997 |
| WO | 9839639 | 9/1998 |
| WO | WO 99/13346 | 3/1999 |
| WO | 0079266 | 12/2000 |
| WO | 0101056 | 1/2001 |
| WO | 03067275 | 8/2003 |
| WO | WO 2004/004998 | 1/2004 |
| WO | 200506921 | 7/2005 |

OTHER PUBLICATIONS

U.S. Appl. No. 09/815,342, filed Mar. 21, 2001, Van Doren et al.
"Automatic, Computer Controlled, Processing of Advanced Composites"; *Defense Small Business Innovation Research (SBIR) Program*; Apr. 7, 1988; 25 pgs.
Baumgartner et al.; "Computer Assisted Dielectric Cure Monitoring in Material Quality and Cure Process Control"; *SAMPE Journal*; Jul./Aug. 1983; pp. 6-16.
Buczek; "Considerations in the Dielectric Analysis of Composites"; *40th International SAMPE Symposium*; May 8-11, 1995; pp. 696-710.
Buczek; "Self-Directed Process Control System for Epoxy Matrix Composites"; *40th International SAMPE Symposium*; May 8-11, 1995; 8 pgs.
"Critical Point Control/Statistical Quality Control Software Module"; *Micromet Instruments*; 1993; 2 pgs.
Desanges; "Changes in the Electrical Properties of Natural Rubber/Carbon Black Compounds During Vulcaniation"; *Revue Generale du Caoutchouc*; Dec. 1957; 34(12); pp. 631-649.
"Dielectric Cure Testing on Polyester Bulk Molding Compound"; *Holometrix Micromet*; 2001; 3 pgs.; http://www.holometrix.com/holometrix/m_materialtest.asp.
"Dielectric Sensors"; *NETZSCH*; Feb. 21, 2002; pgs.
"Eumetric System III Microdielectrometer . . . "; *Holometrix Micromet*; 2001; 5 pgs.
"ICAM-1000—In-mold Monitoring For SPC, SQC, and CPC (Critical Point Control) of Thermoset Molding Operations"; *Micromet Instruments, Inc.*; at least as early as Mar. 1990; 4 pgs.
"ICAM-1000 Industrial Cure Analysis & Monitoring System"; *Micromet Instruments, Inc.*; Aug. 1, 1991; 1 pg.
"ICAM-2000 Multi-Channel Cure Analyzer"; *Micromet Instruments*; 1993; 2 pgs.
Johnson et al.; "Production Implementation of Fully Automated, Closed Loop cure Control for Advanced Composite Strucutres"; *34th International SAMPE Symposium*; May 8-11, 1989; pp. 373-384.
Keller et al.; "Computer Controlled Processing of Composites Utilizing Dielectric Signature Curves"; *SAMPE Journal*; Sep./Oct. 1992; 28(5); pp. 25-33.
Keller et al.; "Real Time, In-Situ Dielectric Monitoring of Advanced Composites Curing Processes"; *Programmed Composites, Inc.*; Aug. 1, 1987; 63 pgs.

Khastgir; "A Comparative Study of Step Curing and Continuous Curing Methods"; *Rubber World*; Jan. 1994; pp. 28-31.

"Lockheed Signature Process Control for Composites Proposal"; *Ketema Programmed Composites, Inc.*; Jul. 1, 1993; pp. 1-12.

"MDE Series 10 Cure Monitor"; *Holometrix Micromet*; at least as early as Mar. 15, 2000; 2 pgs.

"Mono-Probe"; *TYT-NAM-MON*; Oct. 27, 2000; 1 pg.

"Northrop Aircraft Division RTM System Proposal"; *Ketema Programmed Composites, Inc.*; Apr. 1, 1993; 13 pgs.

"Notification of Transmittal of the International Search Report or the Declaration" from the Patent Cooperation Treaty in International Patent Application No. PCT/US02/32480 filed Oct. 9, 2002.

O'Conor et al.; "Update to the Jun. 1990 Confidential Descriptive Memorandum"; *Micromet Instrument, Inc.*; Dec. 1, 1990; 17 pgs.

Persson; "A Novel Method of Measuring Cure—Dielectric Vulcametry"; *Plastics and Rubber Processing and Applications*; 1987; 7(2); pp. 111-125.

"Product Selection Grid"; *Holometrix Micromet*; 2001; 1 pg.; http://www.holometrix.com/holometrix/m_prgrid.asp.

Rajeshwar; "AC Impedance Spectroscopy of Carbon Black-Rubber Composites"; *Department of Chemistry and Biochemistry at The University of Texas as Arlington*; Sep. 21-24, 1999; 13 pgs.

SmartTrac Advertisement, *Automotive News*; May 21, 2001, 1 pg.

"SmartTrac"; *Innovative Aftermarket Systems, Inc.*; 2001; 2 pgs. http://www.ias-inc.net/pages/products/smart.html.

"Textron Aerostructures Autoclave Process Control Proposal"; *Ketema Programmed Composites, Inc.*; Feb. 12, 1993; 16 pgs.

"The Eumetric System III Microdielectrometer"; *Micromet Instruments, Inc.*; Sep. 1991; 4 pgs.

"Thermokinetics"; *NETZSCH*; ; Nov. 8, 2001; 2 pgs.

"Tool Mount Sensors"; *NETZSCH*; Feb. 21, 2002; 2 pgs.

"Vulcanization of Natural Rubber"; *NETZSCH*; Nov. 8, 2001; 2 pgs.

U.S. Appl. No. 11/077,915, filed Mar. 11, 2005, Schneider et al.

Day; "Cure Characterization of Thick Polyester Composite Structures Using Dielectric and Finite Difference Analysis"; *Composite Material Technology; ASME*; 1993; PD-vol. 53:249-252.

Prepreg Cure Characterization Using Simultaneous Dynamic Mechanical Analysis-Dielectric Analysis (DMA-DEA); *Perkin Elmer Thermal Analysis Newsletter*; (date unknown); 4 pp.

"Tool Mount Sensors"; http://www.micromet.com/home/rds.htm; (date unknown); 2 pp.

"Wellons True Capacitance Moisture Meter System" Wellons, Inc. 2005; 1 page.

Wagner Electronics-Press Releases.

James "Dielectric Properties of Lumber Loads in a Dry Kiln" United States Department of Agriculture, Research Paper FPL 436; 1983; p. 1-16, cover, abstract and final page (19 pages total).

James et al. "In-Kiln Moisture Monitoring Systems" In: Robertson, Doris, coord. Computer automation for sawmill profit: Proceedings 7333: Oct. 4-6, 1982; Norfolk, VA. Madison, WI: Forest Products Research Society; 1984: p. 91-94.

English Translation of the First Office Action for Chinese Patent Application No. 02829296.0, issued Nov. 17, 2006.

\* cited by examiner

LEGEND:

o  Data Point: coordinates being (for a given curing condition): Evaluator 6 determined time, and a corresponding rheometrically determined cure time.

——  Best Fit through the Data Points

- - - -  95% Confidence Intervals

LEGEND:

o    Data Point: coordinates being (for a given curing condition): a determined time from a selected four-term multiple regression instance of Equation 2, and a corresponding rheometrically determined cure time.

—— Best Fit through the Data Points

- - - - 95% Confidence Intervals

Fig. 16
Conditions and Rheometry for Natural Rubber Designed Experiment

| temperature (deg C) | accelerator loading | T90 (sec) |
|---|---|---|
| 165 | low | 225 |
| 175 | low | 145 |
| 185 | low | 99 |
| 165 | nominal | 210 |
| 175 | nominal | 131 |
| 185 | nominal | 88 |
| 165 | high | 154 |
| 175 | high | 104 |
| 185 | high | 78 |

Fig. 17
Correlation between Algorithm and Rheometry within Natural Rubber Designed Experiment

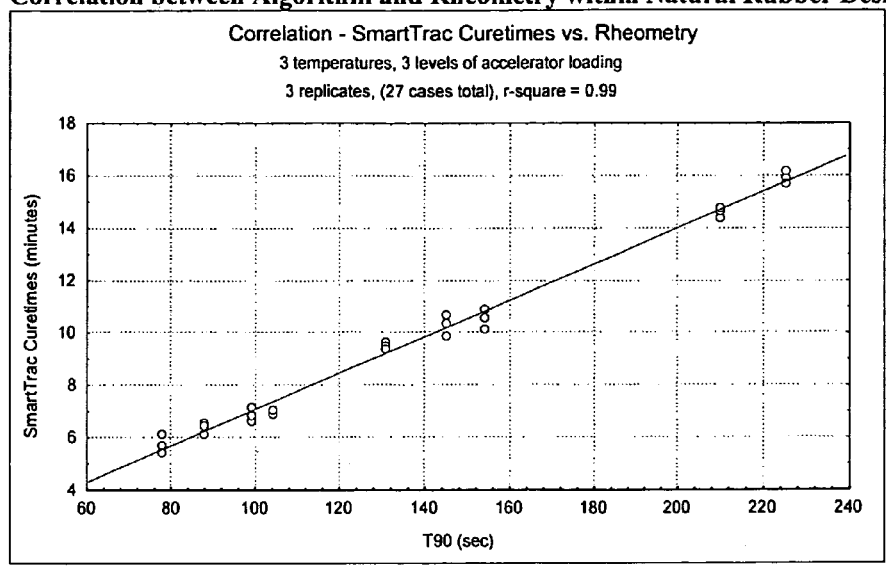

LEGEND:

o   Data Point: coordinates being for (a given curing condition): a determined time from a selected four-term multiple regression instance of Equation 3, and a corresponding rheometrically determined cure time.

—— Best Fit through the Data Points

----- 95% Confidence Intervals

Fig. 18
Conditions and Rheometry for Broad Sampling of Natural Rubber Batches

| Batch ID | Cure Characteristic | Hardness | Temp (C) | T90 (sec) |
|---|---|---|---|---|
| AA22120-1 | slow curing | nominal | 165 | 225 |
| AA22120-1 | slow curing | nominal | 175 | 144.6 |
| AA22120-1 | slow curing | nominal | 185 | 99 |
| AA12120-5 | nominal-production | nominal-production | 165 | 210 |
| AA12120-5 | nominal-production | nominal-production | 175 | 130.8 |
| AA12120-5 | nominal-production | nominal-production | 185 | 90 |
| AA32120-1 | fast curing | nominal | 165 | 153.6 |
| AA32120-1 | fast curing | nominal | 175 | 103.8 |
| AA32120-1 | fast curing | nominal | 185 | 78 |
| AA12259-1 | nominal | soft | 165 | 199.8 |
| AA12259-1 | nominal | soft | 175 | 123.6 |
| AA12259-1 | nominal | soft | 185 | 89.4 |
| AA12189-1 | nominal | hard | 165 | 189.6 |
| AA12189-1 | nominal | hard | 175 | 123.6 |
| AA12189-1 | nominal | hard | 185 | 88.2 |
| AA12120-15 | nominal-production | nominal-production | 165 | 183 |
| AA12120-15 | nominal-production | nominal-production | 175 | 121.2 |
| AA12120-15 | nominal-production | nominal-production | 185 | 84.6 |
| AA12120-23 | nominal-production | nominal-production | 175 | 120 |

LEGEND:

o   Data Point: coordinates being (for a given curing condition): a determined time from a selected four-term multiple regression instance of Equation 3 for natural rubber, and a corresponding rheometrically determined cure time.

—— Best Fit through the Data Points

----- 95% Confidence Intervals

Fig. 20

| | TEMPERATURE | | |
|---|---|---|---|
| | 165 C | 175 C | 180 C |
| AA22120-1 slow curing | 6 samples 11:10 (predicted cure time) | 6 samples 8:10 (predicted cure time) | |
| AA12120-57 production batch | 4 samples 10:46 (predicted cure time) | 7 samples 7:52 (predicted cure time) | |
| AA12120-58 production batch | | 6 samples 7:56 (predicted cure time) | 8 samples 7:05 (predicted cure time) |
| AA32120-1 fast curing | 7 samples 9:11 (predicted cure time) | 5 samples 7:13 (predicted cure time) | 8 samples 6:09 (predicted cure time) |

BATCH IDENTIFIER

PROCESS AND APPARATUS FOR IMPROVING AND CONTROLLING THE VULCANIZATION OF NATURAL AND SYNTHETIC RUBBER COMPOUNDS

RELATED APPLICATIONS

The present application is a continuation-in-part of U.S. application Ser. No. 10/666,433 filed Sep. 18, 2003 now abandoned; U.S. application Ser. No. 10/666,433 is a continuation-in-part of U.S. application Ser. No. 10/267,197 filed Oct. 8, 2002 now U.S. Pat No. 6,855,791; and is a continuation-in-part of U.S. application Ser. No. 10/102,614 filed Mar. 19, 2002 (now U.S. Pat. No. 6,774,643): and is a continuation-in-part of U.S. application Ser. No. 09/815,342 filed Mar. 21, 2001 now abandoned; U.S. Pat. application Ser. No. 10/267,197 claims the benefit of U.S. application Ser. No. 60/394,736 filed Jul. 9, 2002: U.S. application Ser. No. 10/102,614 claims the benefit of U.S. application Ser. No. 60/278,034 filed Mar. 21, 2001.

RELATED FIELD OF THE INVENTION

This invention relates to a new and improved process and apparatus for monitoring and controlling the vulcanization of natural and synthetic rubber compounds containing fillers such as carbon black, oils, clay, and the like. Typical base rubber polymers which may be employed include styrene-butadiene, polybutadiene, polyisoprene, ethylene-propylene, butyl, halobutyl, nitrile, polyacrylic, neoprene, hypalon, silicone, fluorcarbon elastomers, polyurethane elastomers, natural rubber and hydrogenated nitrile-butadiene rubber, and mixtures thereof.

BACKGROUND OF THE INVENTION

Heretofore methods of applying fixed process parameters to the processing of rubber polymeric compounds during vulcanization have resulted in both reduced productivity due to overly conservative cure times and poor product uniformity due to the inability of the fixed process parameters to accommodate the inherent variability in the process.

The relationship of dielectric properties and the state and rate of the cure of polymers is well known. Related publications, incorporated herein fully by reference, in this field are:

U.S. PATENT DOCUMENTS

| | | |
|---|---|---|
| 4,344,142 | August 1982 | Diehr, II et al. |
| 4,373,092 | February 1983 | Zsolnay |
| 4,399,100 | August 1983 | Zsolnay, et al. |
| 4,423,371 | December 1983 | Senturia, et al. |
| 4,496,697 | January 1985 | Zsolnay, et al. |
| 4,510,103 | April 1985 | Yamaguchi, et al. |
| 4,551,807 | November 1985 | Hinrichs, et al. |
| 4,723,908 | February 1988 | Kranbuehl |
| 4,777,431 | October 1988 | Day, et al. |
| 4,773,021 | September 1988 | Harris, et al. |
| 4,868,769 | September 1989 | Persson, et al. |
| 5,032,525 | July 1991 | Lee, et al. |
| 5,219,498 | June 1993 | Keller, et al. |
| 5,317,252 | May 1994 | Kranbuehl |
| 5,486,319 | January 1996 | Stone, et al. |
| 5,528,155 | June 1996 | King, et al. |
| 5,872,447 | February 1999 | Hager, III |

OTHER PUBLICATIONS

Changes in the Electrical Properties of Natural Rubber/Carbon Black Compounds during Vulcanization, 1957, H. Desanges, French Rubber Institute

*A novel method of measuring cure—dielectric vulcametry,* 1986, Sture Persson, The Plastics and Rubber Institute, England

*A comparative study of step curing and continuous curing methods,* 1994, D. Khastgir, Indian Institute of Technology

*AC Impedance Spectroscopy of Carbon Black-Rubber composites,* 1999, K. Rajeshwar, University of Texas at Arlington The prior art has clearly established a relationship between the dielectric (herein also referred to as "impedance") properties of polymeric resins and the curing of such resins. For example, these resins exhibit rheometric and chemical behavior such as melt, volatile release, gelation, and crosslinking that can be recognized by dielectric changes. However, unlike polymeric resins, rubber polymeric compounds do not melt or exhibit gelation during cure or vulcanization and are therefore much more difficult to characterize, monitor and control by analysis of dielectric characteristics. Moreover, none of the prior art associated with polymeric rubber curing (also referred to as "vulcanization") addresses the practical aspects of taking measurements directly in the production process, especially in the highly abrasive and high pressure environment of injection molding. Additionally the prior art does not show how to use the electrical data obtained to achieve closed-loop control of the curing or vulcanization process of, e.g., polymeric rubber over a wide range of molding methods and conditions.

The prior art also does not show how to compensate, in the vulcanization process: (a) for variations in polymeric rubber curing compounds from batch to batch and within batches, and (b) for differences in vulcanizate thickness. Additionally, the prior art does not compensate for additional variables, which are introduced into the vulcanization process by the nature of the vulcanization equipment, tooling, and thermal history of polymeric rubber curing compounds.

Moreover, the prior art uses dielectric or impedance measuring apparatus, which employ opposing and parallel electrodes of precise area and separation distance, and in which, the electrodes are in direct contact with the rubber compound. Although such electrodes and apparatus provide a means for measuring impedance properties during cure, they are entirely impractical for use in a production environment. For example, many rubber components are produced using injection molding technology which subjects the sensors to pressures up to 30,000 psi and temperatures up to 425° F. Moreover, due to the flow inside the mold during injection, in addition to the carbon and silica fillers present in many rubber compounds, the sensor must survive in a highly abrasive environment. Finally, the sensor must also be able to survive mold cleaning via typical cleaning methods such as $CO_2$ and plastic bead blast.

Accordingly, it is desirable to have an apparatus and method for alleviating the above described drawbacks to using impedance data measurements for monitoring and controlling the vulcanization process for rubber polymeric compounds. In particular, it is desirable for the impedance sensor provided at the vulcanization equipment to be both extremely rugged and more easily used in that the electrodes: (a) need not be of precise area, (b) need not be of precise separation distance from one another, and (c) need not be in direct contact with the material being vulcanized. In addition, it would be desirable to have a method for correlating the desired properties of a rubber polymeric compound product with impedance measurements.

DEFINITIONS AND TERMS

Numerous technical terms and abbreviations are used in the description below. Accordingly, many of these terms and abbreviations are described in this section for convenience. Thus, if a term is unfamiliar to the reader, it is suggested that this section be consulted to obtain a description of the unknown term.

Rubber Polymeric Compounds (equivalently, "Polymeric Rubber Compounds", and "Rubber Compounds" herein): Typical base rubber polymeric compounds including (but not limited to) styrene-butadiene, polybutadiene, polyisoprene, ethylene-propylene, butyl, halobutyl, nitrile, polyacrylic, neoprene, hypalon, silicone, fluorcarbon elastomers, polyurethane elastomers, natural rubber and hydrogenated nitrile-butadiene rubber (HNBR), and mixtures of such rubber compounds having fillers such as recited hereinabove.

ODR: Oscillating Disk Rheometer—A device that measures the rheological characteristics (elastic torque, viscous torque, etc.) of a polymer during vulcanization, using an oscillating disk to apply stress to the curing polymer.

MDR: Moving Die Rheometer—A device that measures the Theological characteristics (elastic torque, viscous torque, etc.) of a polymer during vulcanization, using a moving die to apply stress to the curing polymer.

Rheometric instrument: A device that measures the Theological characteristics (elastic torque, viscous torque, etc.) of a polymer during vulcanization.

T90 Time: The time, as measured in an ODR or MDR at which a given rubber compound at a given curing temperature, reaches 90% of its ultimate elastic torque value.

Designed Experiment: A single set of related experiments drawn up from one of the types of designs to be found in the body of methods for design of experiments described hereinbelow in the Detailed Description.

Exponential Dampening: The damping coefficient ( ) as defined by a best exponential fit to a set of raw data, where the fit curve (y) is described by the equation:

$y = Ae^{-\alpha t}$, where t is time.

Exponential Amplitude Coefficient: The amplitude coefficient (A) as defined by a best exponential fit to a set of raw data, where the fit curve (y) is described by the equation $y = Ae^{-\alpha t}$, where t is time.

Topological Features of Impedance Related Data: Recognizable and distinct features within a cure curve, such as a peak (maxima), valley (minima) or flat (no slope).

Low CTE Metallic Material: A material with a low coefficient of thermal expansion.

Tool Steel: A steel suitable for use in making injection and compression molds such as AISI Type A2 Tool Steel.

Witness cavity: A small cavity attached to but separate from injection mold for the rubber polymeric compound part being produced, wherein this small cavity is for allowing in-mold vulcanization sensor measurements of a rubber compound cure without the sensor being in direct contact with the curing part. In particular, a dielectric sensor in the witness cavity does not directly sense any of the parts that are being produced. Instead, the sensor monitors the cure of the rubber polymeric compound in the witness cavity.

R-square ($R^2$): R-square (also known as the coefficient of determination) is a statistical measure of the reduction in the total variation of the dependent variable due to the independent variables. An R-square close to 1.0 indicates that a model (also referred to herein as an "algorithm") accounts for almost all of the variability in the respective variables.

Confidence interval: A range of values within which a particular number of interest is desired to be, at some specific level of probability such as 95%.

SUMMARY OF THE INVENTION

The present invention is a method and system for controlling the vulcanization (herein also denoted "curing") of rubber polymeric compounds. In particular, the present invention includes novel features for monitoring the polymerization and determining in real-time the optimum cure time for the production of parts made from rubber polymeric compounds (herein also denoted as "polymeric rubber compounds" or merely "rubber compounds"). According to the present invention, during the curing of rubber polymeric compounds, data streams of impedance values are obtained (denoted herein as "impedance data streams"), wherein these values are indicative of impedance measurements obtained from one or more capacitor circuits (CC). Each of the capacitor circuits is operatively configured so that such a rubber polymeric compound becomes part of the capacitor circuit, and in particular, becomes a dielectric for the circuit. For each of the impedance data streams there is a corresponding graphical representation for presenting the particular impedance properties versus time that are provided by the impedance data stream. Such graphs are denoted "process curves" herein, and each such process curve is generally identical in informational content to the impedance data stream from which the process curve is derived. Accordingly, many embodiments of the present invention utilize derived characteristics of the impedance data streams that is more easily described in terms of their graphical representations as process curves, e.g., shape and/or geometric curve characteristics such as slopes and/or an area under such a process curve. Note that such impedance data streams can be representative of a time series of one or more of the following impedance types of impedance values: the impedance (Z), phase angle (ø), resistance (R), reactance (X), conductance (G), and/or capacitance (C). Thus, the impedance data streams (and their related process graphs) are derived from the signal responses output by the activation of one or more of the capacitor circuits CC, wherein such activation is the result of at least one, and more generally, a plurality of signals of different frequencies being input to such capacitor circuit(s). Thus, in some embodiments of the present invention, each of the process curves may be obtained from a single, and in general different, signal frequency input to the capacitor circuit(s), and the coffesponding shape (or other computational characteristics) of each of the process curves may be used in monitoring, controlling and/or predicting an outcome of a curing process for polymeric rubber compounds.

In some embodiments of the present invention, various time series capacitor circuit output data components (i.e., impedance (Z), phase angle (ø), resistance (R), reactance (X), conductance (G), or capacitance (C)) are separately processed, thereby resulting in a process curve with distinctive shape (or other features) for each of these components.

Accordingly, it is an aspect of the present invention that such features from impedance (Z), phase angle (ø), resistance (R), reactance (X), conductance (G), or capacitance (C) graphs (e.g., plotted versus time) can be used for monitoring and controlling the cure time by measuring a portion of the process curve and calculating or predicting the optimum cure time. Thus, since a particular shape (or other "computational features" such maxima, minima, slope, rate of slope, portion having substantially zero slope, inflection point, the area under a portion of the curve, etc.) of such process curves may be substantially repeatable for curing a particular rubber polymeric compound or material, such features can be effectively utilized in a mass production environment for producing consistently high quality cured products (e.g., seals, gaskets, and tires).

Moreover, it is a further aspect of the present invention that for a given rubber polymeric material to be cured, the present invention can identify at least some of the computational features of these process curves substantially independently of the configuration of the product being produced by utilizing dielectric properties obtained from a "witness cavity" incorporated into the runner system (i.e., the flow path within the mold that channels the rubber to the product cavities) of the mold, as one skilled in the art will understand. In particular, such computational features can be correlated with the chemical and rheometric changes occurring during the curing process.

Thus, although such process curves may vary in amplitude and duration (e.g., due to cured part thickness, thermal history, mold temperature and heat rate, curative level, compound batch variations, and various other factors), the present invention may be used for monitoring, controlling and/or predicting cure states of products in a mass production environment wherein the products being produced may be subject to significant process and rubber compound variation.

For example, for a particular sample or product to be cured, properties of one or more of the above described process curves can be calculated for a specific measurement period wherein a portion of the data corresponding to each process curve of the sample may be correlated to a desired final cure state of the product. Thus, such a correlation can be used to establish a time for appropriately curing a part in production, wherein the part is substantially identical to the sample. In particular, the present invention predicts cure times as will be described more fully herein below.

In one embodiment of the present invention, it has been found that during the curing of a polymeric rubber compound, there is a distinctive capacitance versus time process curve, and/or a distinctive conductance versus time process curve produced. Thus, for a part molded from a particular rubber polymeric compound, the shape of at least one of the corresponding distinctive capacitance and/or conductance process curves (for the particular rubber polymeric compound) may be consistent enough for predicting the state of the part during vulcanization. Thus, although such process curves for individual parts may vary in amplitude and time ordinates (principally due to part thickness, thermal history, mold temperature and heat rate, curative level, and various other factors), the general shape of such curves can be used in predicting the state of vulcanization. That is, the shape of such process curves can be correlated to the chemical and physical changes occurring during the curing process.

For example, the initial slope of at least one of the distinctive capacitance and conductance process curves for a rubber compound being cured is associated with the rate of the curing reaction and this initial slope can be used to establish or predict the preferred or correct cure time for the polymeric rubber part being produced. In addition, the area under such a process curve or a portion of the process curve may be associated with the cure "energy" and can be also be used to control or predict the cure time. For certain rubber compounds, one or more of the capacitance and conductance process curves exhibit a shape including a "VALLEY" and/or a "PEAK" which can be used to control or predict the cure time. Moreover, it is an aspect of the present invention to employ software algorithms for identifying process curve features, wherein such algorithms compute process curve characteristics such as linear fit coefficients, polynomial fit coefficients, and logarithmic fit coefficients so that these computed characteristics can be used to control the cure time and thereby achieve a desired part property such as a predetermined range of tensile strength and/or compression set.

In one embodiment, the present invention (FIG. 1) includes an equipment enclosure 5 having the following high level components:

(1.1) Data acquisition hardware (e.g., data acquisition card 35 as shown in FIG. 13), and control hardware (e.g., for implementing the control system 39, also shown in FIG. 13, thereon);

(1.2) A host computer 9 with human machine interface software, and signal conditioning and control software.

Additionally, FIG. 1 shows vulcanizing equipment 45 having the following high level component:

(1.3) Capacitor 68 formed from: (i) impedance sensor(s) 17 which is placed directly adjacent to the rubber compound 16 being vulcanized, (ii) a grounded capacitor plate 64, and (iii) the rubber compound 16 as the capacitor dielectric.

Furthermore, this embodiment may include an expert system and/or rule base software for recognizing topographical features or mathematical properties and/or patterns of the impedance process curve(s).

The data acquisition and control hardware of the embodiment of FIG. 1 provides a means to generate a plurality of sinusoidal signals of various frequencies, which are multiplexed onto the impedance sensor 17. The frequency range applied then allows for a spectrum of conductance and capacitance measurements to be captured as output from the impedance sensor 17. Thus, the conductance and capacitance readings (equivalently, process curves) are specific to the rubber polymeric compound under cure, in that the dipolar and/or carbon constituents of the compound will generate a pattern of dielectric responses specific to the rubber polymeric compound. Accordingly, a high level representation of an algorithm that uses such readings of impedance characteristics for controlling the vulcanization process is shown in FIG. 2.

Note that in the present embodiment of the invention (i.e., FIG. 1), each impedance sensor 17 includes a primary electrode 10 (FIG. 3) that serves as a capacitor plate for the capacitor 68. An additional electrode 111 rings the primary electrode 10 and acts as a shield that precludes excessive fringing of the electrical field to the adjacent tool surface in which the sensor 17 is typically flush mounted. Both electrodes 10 and 111 are embedded in a ceramic body (not shown) and are separated from the rubber polymeric compound 16 being evaluated by a thin layer of alumina ceramic 13 or other suitable material, which is dielectrically stable over the temperature range of the vulcanizing process. Any other planar or semi-planar conductive surface within the production process (typically an opposing mold surface) can serve as the opposing plate (i.e., ground plate 64) of the capacitor 68 and acts as the third electrode for capacitively coupling with the primary electrode 10. Thus, since the opposing plate is grounded, when a complex current is driven through a resistor 19 (FIG. 3) to ground, this current passes through the rubber compound 16 which is the dielectric within the formed capacitor. The complex voltage across the resistor 19 is then measured with a high precision amplifier 36. The resulting signal is then demodulated via software component(s) collectively labeled 23 (FIG. 1) into its complex impedance components (e.g., conductance and capacitance).

It is a further aspect of the present invention, that in various embodiments and for certain rubber compounds, the corresponding shape of one or more of the above described process curves may exhibit a "maxima" and/or a "minima" at a given time which can also be used to infer useful information in monitoring, controlling and/or predicting the proper cure time. It is a further aspect of the present invention that in various embodiments and for certain rubber compounds, one or more (preferably a plurality) of "evaluators" are provided for outputting values related to the cure time of a part. Such evaluators may be for determining, e.g., the corresponding slope or integrated area under one or more of the above described process curves. The output from each of the evaluators can be coffelated with known curing times of rubber compound samples to thereby determine a predictive effectiveness of the evaluator. In one embodiment, the known curing times can be T90 times, T75 times, or T50 times that are determined by obtaining rheometric measurements of the samples during their curing. The evaluators that exhibit a high degree of conelation to physically measured rheometric curing properties of the samples are used to infer useful information in monitoring, controlling and/or predicting the proper cure time of rubber compound molded parts such as parts that are mass produced. In at least one embodiment of the present invention, the output from two or more (e.g., four) evaluators providing the highest degree of correlation with the measured rheometric curing properties are combined (e.g., as a linear combination) to yield an even better predictor for predicting part curing times.

It is a further aspect of the present invention that embodiments thereof include signal processing and other software and hardware ("components") for both deriving such computational features (e.g., maxima and/or minima) of the process curves obtained from a rubber polymeric compound being cured, and utilizing such features to determine, in real-time, the optimum cure time for each production cure cycle.

Moreover, it is an aspect of the present invention that such cure times are determined for achieving a desired property such as tensile strength, dynamic stiffness, and/or compression set in the resulting cured part.

Accordingly, the present invention may be described by the following aspects:

Aspect 1: A method for curing a part composed a rubber compound composed of natural or synthetic rubber together with fillers using vulcanization equipment, comprising:
  (a) measuring curing conditions by dielectric or impedance means applied on opposite sides and through the rubber part or a witness cavity representing the part during the curing process to produce a process curve for a specific rubber compound, wherein said process curve is correlated with one or more rheometric properties of the rubber compound and one or more desired or specified mechanical properties of the rubber part;
  (b) analyzing the process curve for the specific rubber compound with a software algorithm which defines and quantifies a correlation relationship between the process curve and the rheometric properties of the rubber compound and the desired or specified part mechanical properties; and
  (c) applying the correlation relationship in real-time to end the curing process and thereby produce rubber part(s) of uniform quality and with reduced process cycle time.

Aspect 2: A method for curing one or more parts, comprising:
  determining, for each evaluator of a plurality of evaluators, a part curing predictive effectiveness;
  wherein for each of said evaluators (E), said step of determining determines, for a plurality of curing conditions, a correspondence between (a1) and (a2) following:
  (a1) outputs by the evaluator E, wherein for each curing condition ($CC_j$) of the curing conditions, there is a portion of the outputs obtained when the evaluator E is provided with a corresponding activation input that includes a sequence of impedance responses from a device providing signals indicative of impedance measurements of a rubber compound (RC), wherein the rubber compound RC is being cured:
    (i) according to the curing condition $CC_j$; and
    (ii) in curing equipment that is also to be used in curing the part, and
  (a2) for each curing condition ($CC_k$) of the curing conditions, a known curing time[DJD1] of a rubber compound for the curing condition $CC_k$;
  providing, for each of a plurality of predetermined frequencies, an electrical current to the device, wherein the device outputs signals indicative of impedance measurements for a rubber compound from which the part is being formed in the curing equipment;
  receiving, for each of said frequencies, an impedance data stream including a sequence of impedance responses from said device during the curing of the part;
  for each of one or more of the curing evaluators, activating the evaluator for obtaining a corresponding result related to a prediction of a cure time of the part, when the evaluator is provided with a corresponding activation input from said impedance data streams;
  using the corresponding results from the one or more evaluators for obtaining a predicted cure time for the part;
  wherein a step of identifying is performed prior to said step of using, and said step of identifying identifies at least one of the evaluators ($E_1$) for predicting a cure time for the part, wherein the predictive effectiveness for $E_1$ is better than the predictive effectiveness of at least one other of the evaluators.

Additional aspects, features and benefits of the present invention will become evident from the accompanying drawings and the detailed description herein below.

BRIEF DESCRIPTION OF THE FIGURES

FIG. 16 shows curing conditions and resulting rheometry data (i.e., T90 data) for samples of a natural rubber in a designed experiment for determining the effects of various curing conditions on cure rates.

FIG. 17 shows the correlation between the algorithm and rheometry within the natural rubber designed experiment.

FIG. 18 shows the conditions and rheometry for a broad sampling of natural rubber batches and temperatures.

FIG. 20 shows average cure times selected by the algorithm under various cure conditions—no porosity observed in any of the algorithm-controlled parts.

DESCRIPTION OF THE PREFERRED EMBODIMENTS

Figure 1:
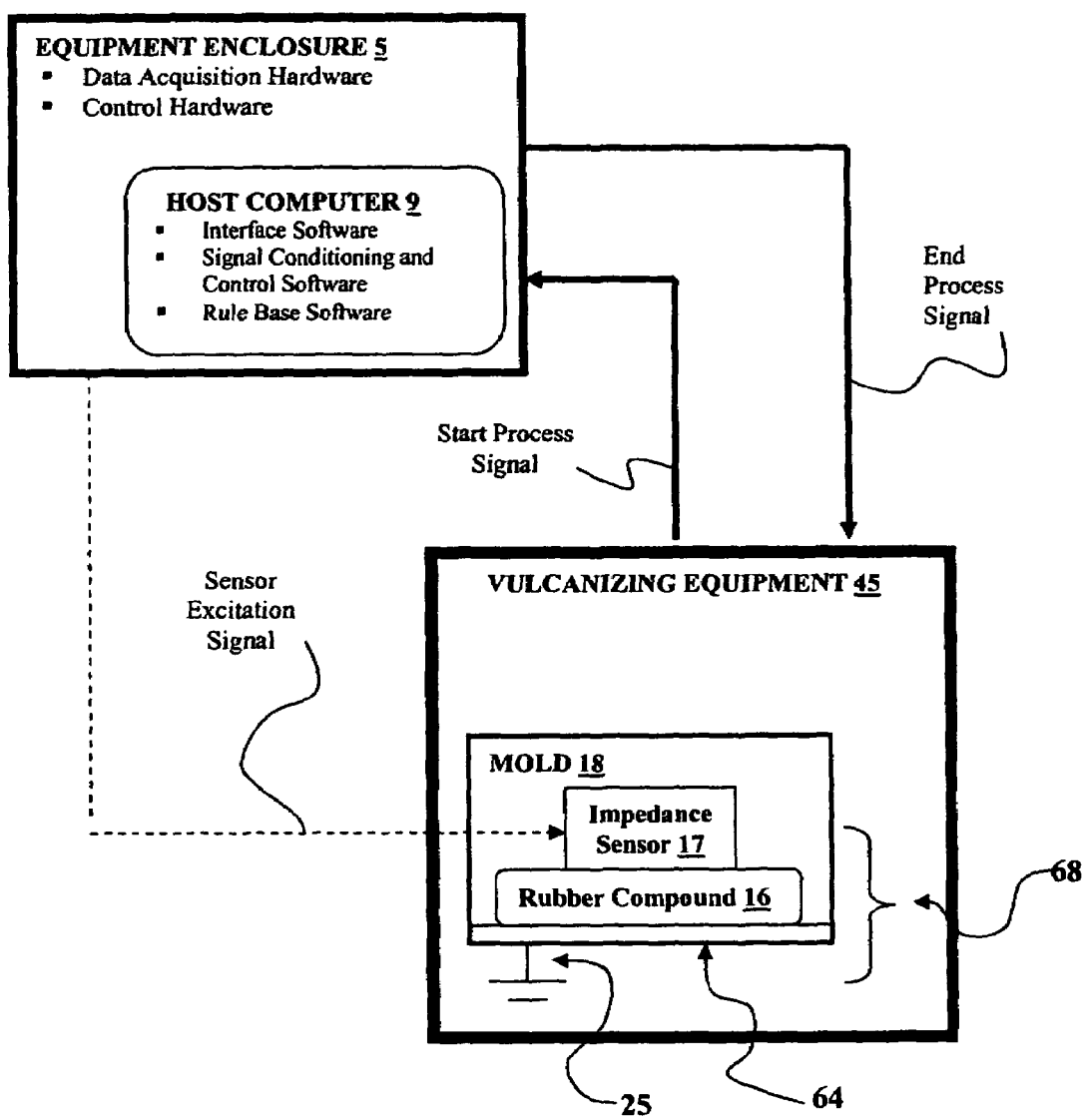
FIG. 1 shows the Invention System Overview Schematic.
Figure 2:
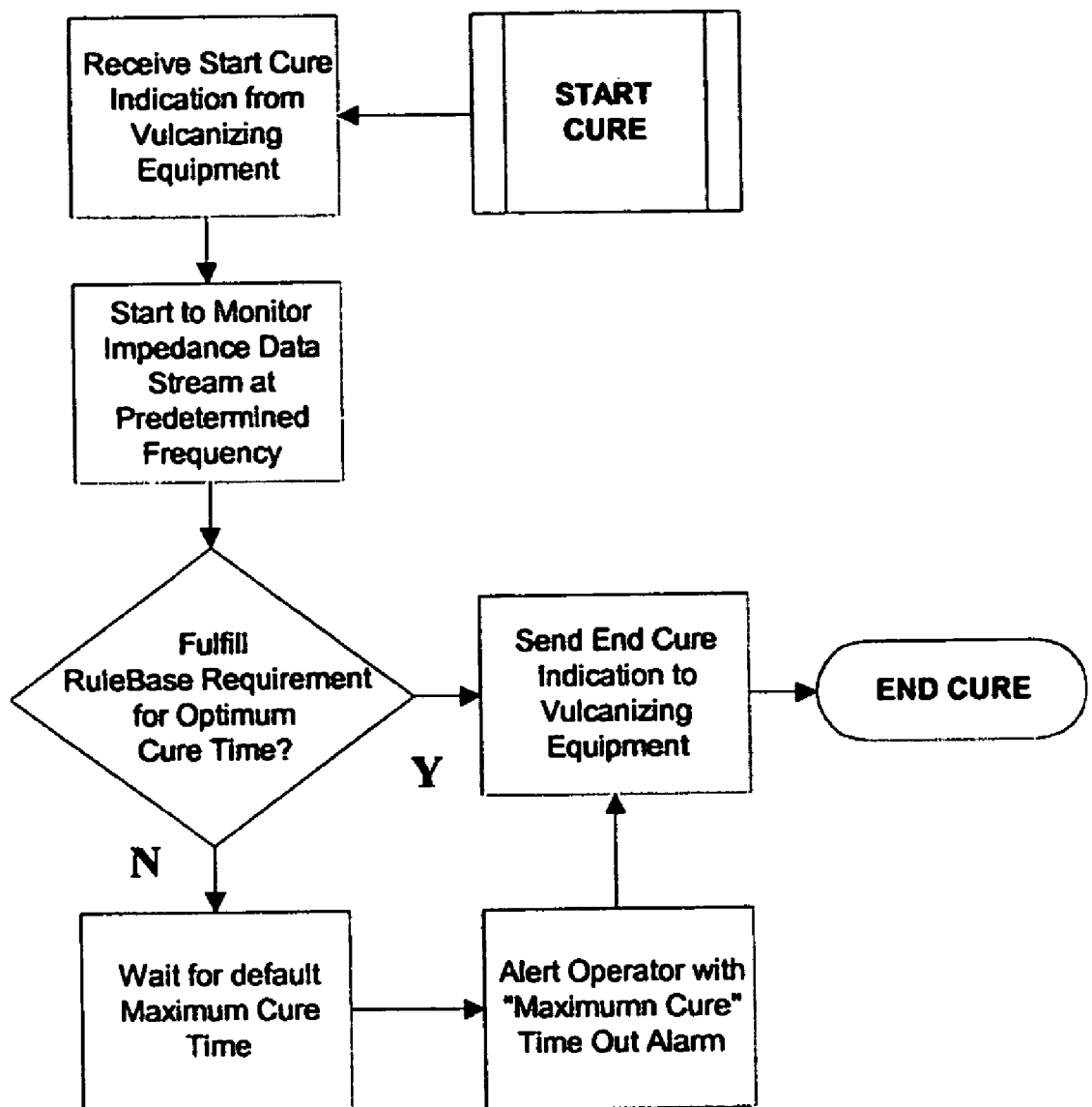
FIG. 2 shows the System Operation and Software Algorithm Control Logic.
Figure 3:
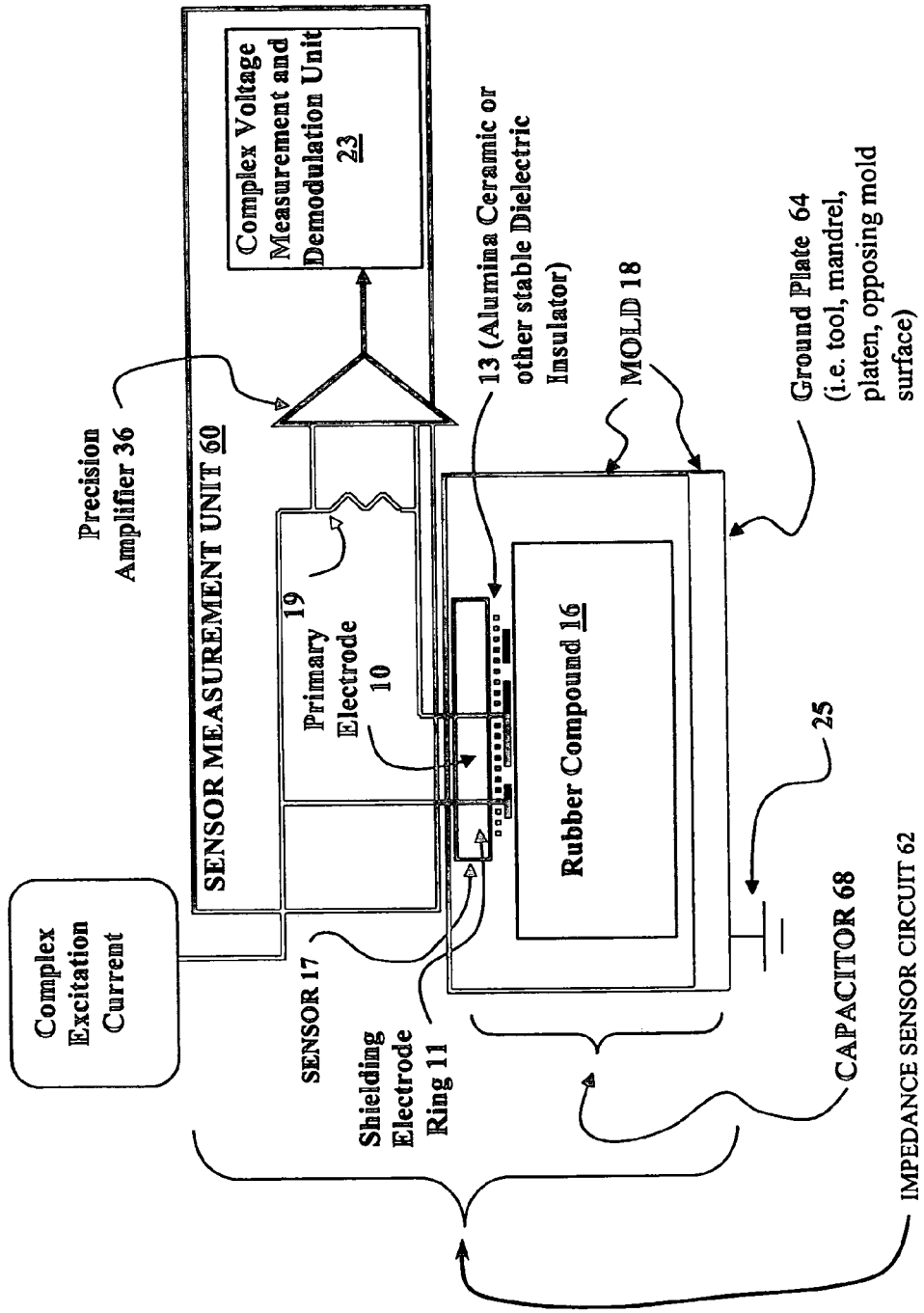
FIG. 3 shows the Impedance Sensor Excitation and Measurement Schematic.
Figure 5:
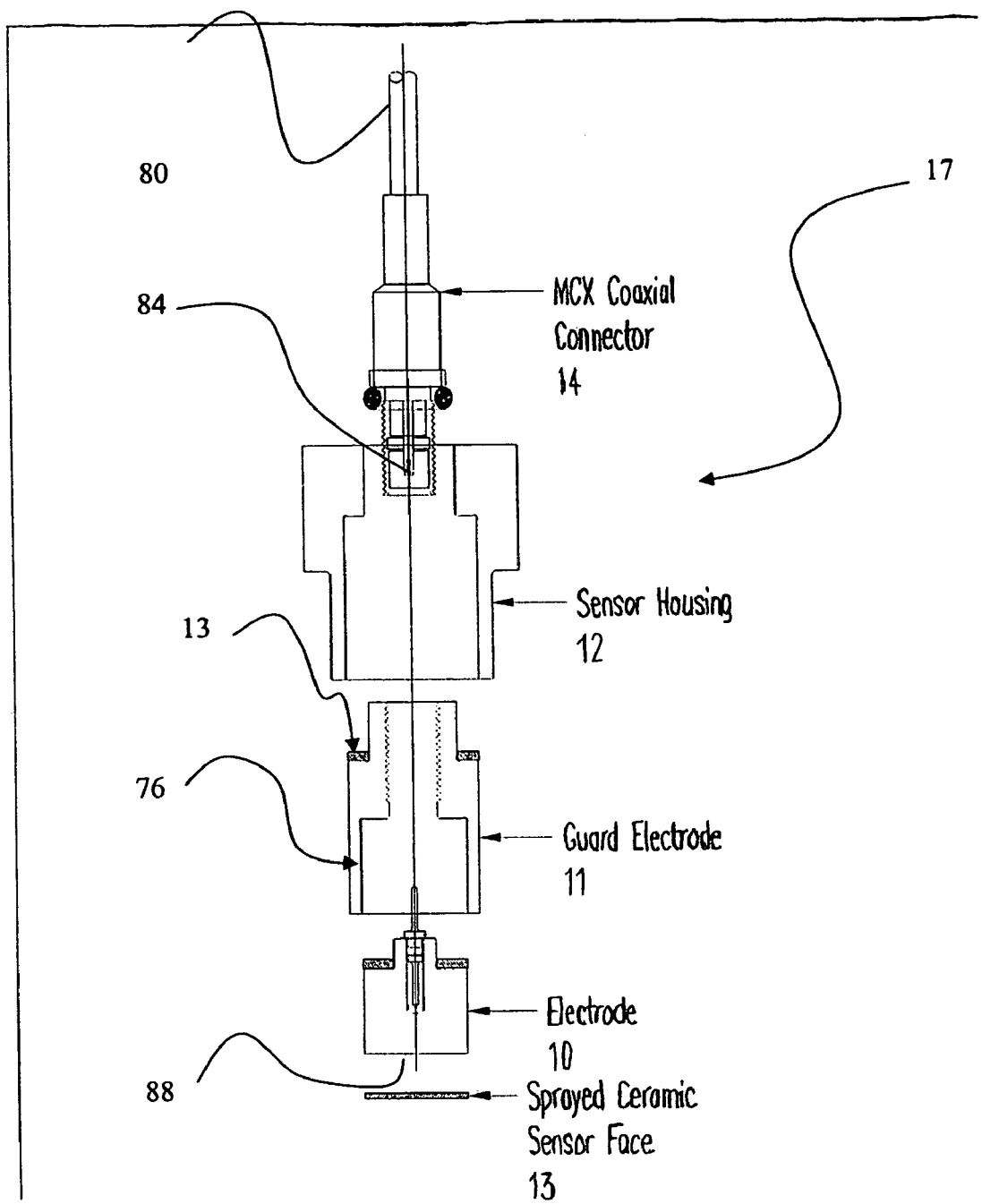
FIG. 5 shows an exploded view of one embodiment of the sensor 17.

Key Components of the Invention:

A representative embodiment of the invention can fundamentally be broken into five key components and/or methods, which together form the equipment, tools and processes necessary for monitoring impedance properties in injection and other rubber compound molds or molding environments such as molds for compression molding, transfer molding, and the like. These components and methods are identified as follows:

(2.1) A production-capable sensor 17 (e.g., FIGS. 1, 3 and 5);

(2.2) A non-bridged sensor measurement unit 60 (FIG. 3);

(2.3) A demodulation method for the sensor signal;

(2.4) A method for establishing curing process control algorithms and/or formulas; and (2.5) A real-time curing control system and method for the mass production of rubber compound molded parts.

Each of these components (2.1) through (2.5) are described hereinbelow.

(2.1) Production-Capable Sensor 17

The prior art uses dielectric or impedance measuring apparatuses that employ opposing and parallel electrodes of precise area and precise separation distance. Additionally, the metallic prior art electrodes are typically in direct contact with the rubber compound 16. Although such electrodes and apparatus provide a means for measuring impedance properties during cure, they are entirely impractical for use in a production environment that mass produces molded rubber compound parts. For example, many rubber components are produced using injection-molding technology that subjects the sensors to pressures up to 30,000 psi and temperatures up to 425° F. Moreover, due to the flow inside the molds during injection, and the carbon and silica fillers present in many rubber compounds, the sensor must survive in a highly abrasive environment. Finally, the sensor must be able to survive mold cleaning via the use of $CO_2$ bead blast, plastic bead blast, and the like.

Accordingly, it is desirable to have a sensor for alleviating the above described prior art sensor drawbacks to obtaining in-situ impedance data for monitoring and controlling a vulcanization process. In particular, it is desirable for the impedance sensor provided at the vulcanization equipment to be both extremely rugged and more easily used than prior art sensors. More precisely, it is desirable that the electrodes need not be of precise area, need not be of precise separation distance from one another, and need not be in direct contact with the rubber compound being vulcanized.

The impedance sensor 17 (e.g., FIGS. 1 and 3) satisfies the above requirements. The sensor 17 includes a primary electrode 10 that serves as a capacitor plate for a capacitor 68. An additional capacitor, acting as a guard or shielding electrode 11, rings the primary electrode 10 of each such sensor 17 (there may be more than one of these sensors). The guard electrode 11, which is excited along with the electrode 10, helps to preclude the electrical field induced at the primary electrode 10 of the sensor 17 from fringing or becoming non-linear, as one skilled in the art will understand. The electrodes 10 and 11 are separated from the rubber compound 16 by a thin (e.g., approximately 0.001 to 0.05 inches) ceramic coating 13 (FIG. 3) such as alumina ceramic or other stable dielectric insulator (e.g., dielectrically stable over the temperature range of the vulcanizing process such as, 300° F. to 425° F.). Both electrodes 10 and 11 may be composed of a low CTE metallic material, such as stainless steels, titanium, a nickel-cobalt-iron alloy called Kovar® (which is a trademark owned by CRS Holdings Inc., a subsidiary of Carpenter Technology Corp. of Wyomissing, Pa.), nickel steels, tool steels, tungsten, super alloys, and soft-magnetic alloys, etc embedded in a layered ceramic circuit (not shown).

An alternative embodiment of the sensor 17 is shown in FIG. 5, wherein this embodiment includes a nested construction of A2 tool steel components including a sensor housing 12, the primary electrode 10, and the guard electrode 11, wherein the electrodes are separated radially by a cyanate ester potting material 76 and axially by a thin ceramic coating 13 such as alumina ceramic or other stable dielectric insulator. The ceramic coating 13 may be applied with a thermal spray process (i.e. detonation gun, plasma, or high velocity ceramic (HVOF) spray process, as is well known to those skilled in the art). The ceramic coating 13 provides: (a) electrical isolation for the electrodes 10 and 11, (b) transmits the compressive loads generated by the curing process to the sensor 17, and (c) separates the electrodes 10 and 11 from the rubber compound 16 being cured. A coaxial cable 80 is connected to the sensor via an MCX connector 14 such as Johnson Components' MCX connector 14, p.n. 133-833-401 manufactured by Johnson's Components located at 299 Johnson Ave S.W., Suite 100, Waseca Minn. 56093 which is screwed into the guard electrode 11. The center conductor 84 mates with a pin machined integral with or press fit into the electrode 10. In some embodiments of the sensor 17 shown in FIG. 5, the primary electrode 10, the guard electrode 11, and the housing 12, along with an alumina ceramic face 13 may be fused together and separated electrically with glass or glass doped with alumina ceramic. Also, in some embodiments of the sensor 17 shown in FIG. 5, the primary electrode 10, the guard electrode 11, and the housing 12 may be coated with a diamond or diamond-like 2 to 4 micron coating such as Casidium as supplied by Anatech Ltd of Springfield, Va., and then press fit together such that the diamond or diamond-like coating provides electrical isolation between these three components, and also between the rubber compound 16 and the face 88 of the sensor 17.

Therefore the production-ready sensor 17 can be an extremely rugged device, capable of survival in a high pressure, high abrasion, and high temperature environment. The fundamental electrical function of the sensor 17 is to act as a guarded or shielded electrode, forming a single plate of the capacitor 68 (FIG. 1).

Any other planar or semi-planar conductive surface within the interior of the vulcanizing equipment 45 (FIG. 1) can serve as the opposing electrode plate 64 (FIGS. 1, 3 and 13) of the capacitor 68. Note that the opposing plate 64 acts as the third electrode of the capacitor 68, and thus the opposing plate electrically couples with the primary electrode 10. Further note that the opposing plate 64 is grounded to electrical ground 25 to provide a common signal reference point.

The vulcanizing rubber compound 16 in the injection mold 18 (FIG. 1) is the dielectric within the formed capacitor 68, since it is sandwiched between the sensor 17 and the opposing capacitor plate 64 (e.g., a surface of the mold 18 or a metallic insert within the part being molded from the rubber compound 16). Since the dielectric properties of the rubber compound 16 change as the compound vulcanizes, the impedance of the formed capacitor 68 changes as well. Thus, the present invention provides a non-invasive method of monitoring and controlling vulcanization in the mold 18.

Figure 4:
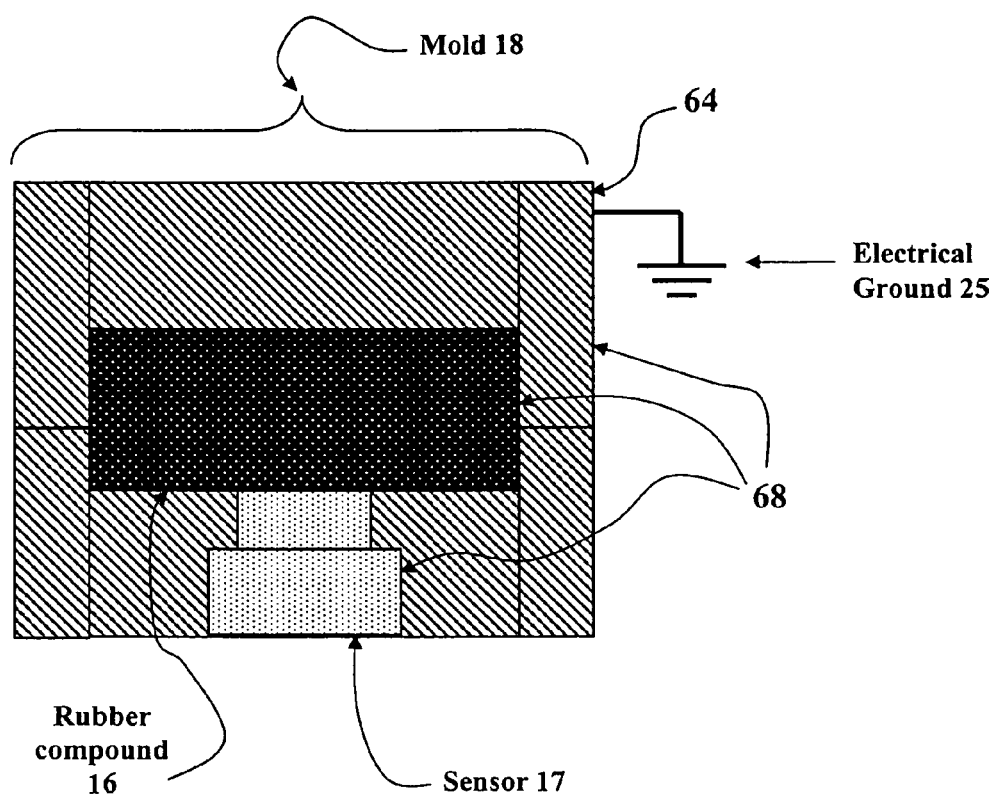
FIG. 4 shows the sensor arrangement schematically in a mold.

FIG. 4 shows how an embodiment of the sensor 17 may be positioned in the mold 18. In particular, the sensor 17 may be flush mounted in the mold 18 so that the sensor is in electrical contact with the part being molded from the rubber compound 16. Alternative locations for the sensor 17 are also within the scope of the present invention. For example, the sensor 17 may be located: (a) in electrical contact with the rubber compound 16 in the runner system feeding the interior of the mold 18, and/or (b) in contact with the rubber compound 16 of a "witness cavity" as described in Definitions and Terms section above. Note that such a witness cavity (not shown) may be particularly important in molding applications where the parts being produced are too small and/or the dimensional specifications are too strict to allow sensor 17 placement directly in contact with the part being produced. However, since the rubber compound 16 in a witness cavity is from the same batch, is subjected to the same mold temperature, and experiences the same heat history as the corresponding rubber compound in the mold 18, the rubber compound of the witness cavity provides a good representation of curing behavior observed in the part itself.

In addition, note that more than one sensor 17 can be used to monitor the curing process of a single part. Moreover, in one embodiment of such a multi-sensor 17 configuration of the present invention, the sensor 17 whose impedance data lags the corresponding impedance data from another of the sensors 17 can be used to control the end point of any given cure cycle.

(2.2) Sensor Measurement Unit 60 (Non-bridged)

Electrical circuits described in the prior art typically include the use of bridge circuits, which are often complex and poorly suited for automation and/or mass production of rubber based parts. Moreover, such bridge circuits typically require an operator to manually balance the bridge, as one skilled in the art will understand.

Figure 6:
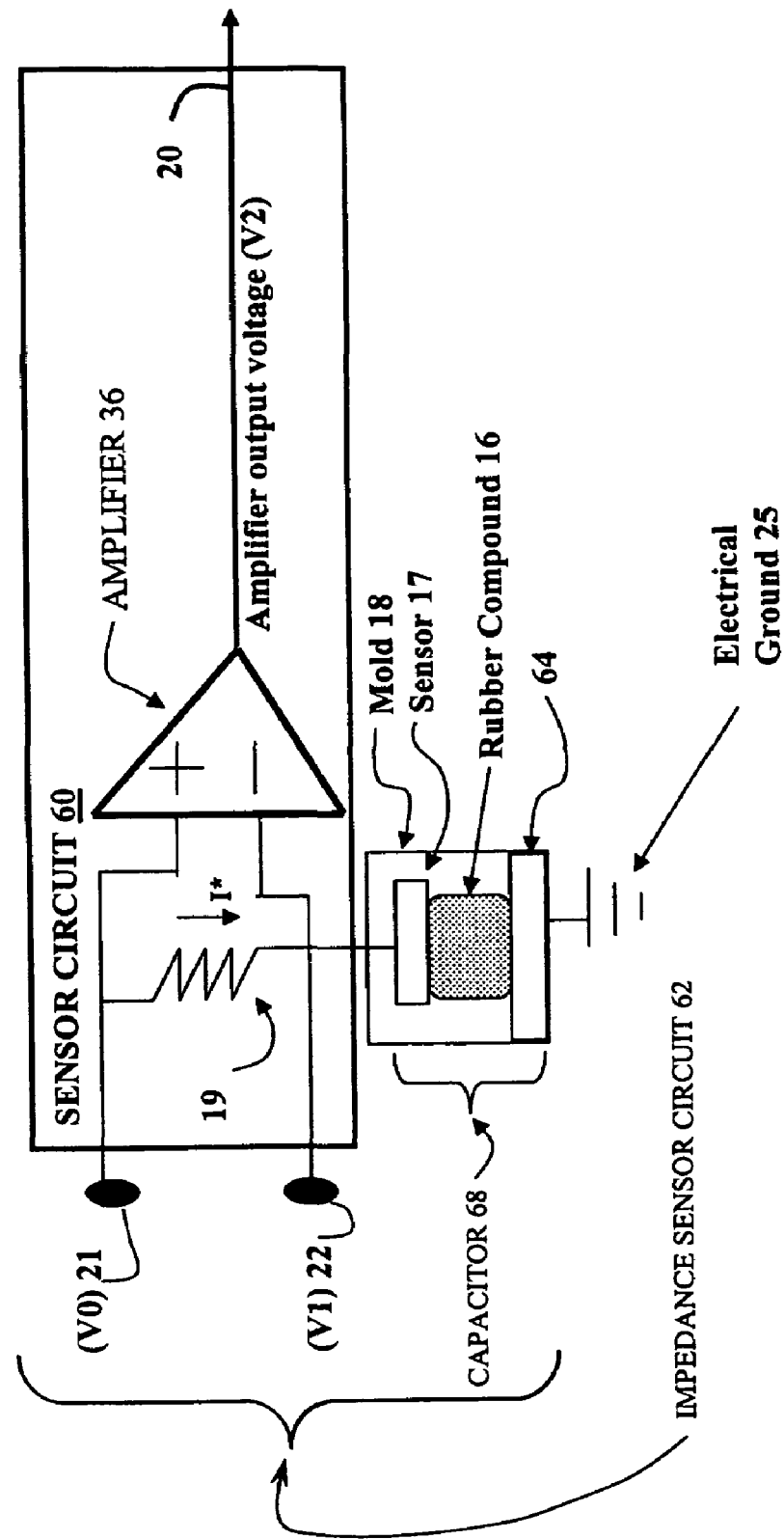
FIG. 6 shows the sensor electrical circuit.

The sensor measurement unit 60 (FIGS. 3, 6 and 13) for the present invention includes a simple voltage divider (FIG. 3) that, in turn, includes the resistor 19. and the complex voltage measurement and demodulation unit 25. The sensor measurement unit is operatively connected to the capacitor 68 formed by sensor 17 and curing rubber 68 for both providing electrical current to the capacitor, and detecting impedance values resulting from the capacitor's response to the electrical signals. Note that the combination of the sensor measurement unit 60 and the capacitor 68 forms an impedance sensor circuit 62. The current provided to sensor circuit 62 is driven to the electrical ground 25 of the mold 18 (via the opposing capacitor plate 64 described hereinabove) through the curing (polymeric) rubber compound 16. The load resistor 19 (typically, having approximately a 200 k-ohm resistance, although a range can be anywhere from 1 kOhm to several Mohms) is placed in line with the flow of current to the sensor 17. The resultant voltage V2 on circuit line 20 (FIG. 6) output by the amplifier 36 measures the voltage across the resistor 19. By simultaneously measuring the applied voltage at position 21 (this applied voltage also known as the "excitation voltage", and also referred to as "V0"), the amount of attenuation and phase shift resultant from the flow of a complex current through the capacitor 68 is determined. FIG. 6 illustrates the sensor electrical circuit 60, where the applied (excitation) voltage at position 21 (e.g., V0=sin ωt) is placed at one terminal of the amplifier 36, and this potential drives a complex current I* through the load resistor 19 (R) and then finally through the capacitor 68 formed by the sensor 17, rubber compound 16, and the electrical ground 25 attached to the mold 18.

The following description assumes a voltage amplitude of 1 volt for the excitation V0 at circuit position 21. However, all the subsequent analysis remains the same if the voltage is not unity, in that for the non-unity cases, the constant "k" in the equations below is defined as the ratio of the negative voltage (V1) at circuit position 22 to the positive voltage (V0) at circuit position 21.

The excitation voltage at position 21 (V0=sin ωt) drives a complex current (I*) through the resistor 19 to ground 25. Accordingly, the voltage V0 is a digitally generated sine wave generated by a high-speed data acquisition card 35 (FIG. 13), such as the PCI-MIO-16E4 card manufactured by National Instruments of Austin, Tex. The data acquisition card 35 produces high quality sinusoidal signals at frequencies varying from 10 Hz to 10 kHz as specified by a user; however, other data acquisition cards 35 are also within the scope of the invention for generating similar or different ranges of frequencies such as the PCI-MIO-16E1 data acquisition card manufactured by National Instruments of Austin, Tex. which can generate and monitor frequencies from 10 Hz to 1.25 MHz. It is also within the scope of the invention to use a simultaneous sampling data acquisition card (e.g., a card specifically designed to carefully preserve interchannel phase relationships) such as the PCI-6110 card manufactured by National Instruments of Austin, Tex.

Upon application of the excitation voltage V0 at circuit position 21, there is a voltage drop that occurs across the load resistor 19, leaving an attenuated and phase shifted signal at the circuit position 22 (i.e., $V1=k\sin(\omega t+\theta)=k<\theta$, where "<" is used to indicate a polar representation of a complex number and denotes the term "at a phase angle of"). The rubber compound 16 between the sensor 17 and electrical ground 25 provides a complex impedance of magnitude Z at phase angle Φ, wherein the phase angle Φ is a property of the curing rubber compound 16, and is not to be confused with the phase angle θ, which is defined as the phase angle difference between V0 and V1.

(2.3) Demodulation of the Sensor Signal.

Calculating Z and Φ is done by simultaneously digitally capturing the excitation signal V0 (e.g., V0=sin(ωt)) and the amplifier 36 output voltage V2 on circuit line 20, where V2=sin(ωt)−ksin(ωt+θ). Alternately, in another embodiment of the invention, the same data could be obtained by capturing the sinusoids V0 ((sin(ωt)) and V1 (ksin(ωt+θ)) directly rather than capturing V2 (sin(ωt)−ksin(ωt+θ)). Note that the previously referenced high-speed data acquisition card 35 can be used to digitize the signals V0 at position 21 and the signals V2 at position 20 thereby preserving the digital representation of the waveforms for further digital signal processing. Note that the values of Z and Φ obtained from the sensor measurement unit 60 as well as the various voltages (e.g., V0 and V2, or alternatively, V0, V1 and V2) from which the values of Z and Φ are derived will hereinbelow be referred to "impedance signal data".

Provided with the digitally preserved signals of V0 and V2, measurement of the quantities k (attenuation) and θ (phase shift) is done via standard demodulation practices, as is understood by one skilled in the art.

Once the quantities k and θ have been measured, determination of Z and Φ is done by analyzing the circuit described in FIG. 6 as follows.
 i. $I^* = (V0 - V1)/R$
 ii. $Z = V1/I^*$
 iii. Substituting, since $V1 = k < \theta$ and $V0 = 1$
 iv. Impedance $(Z)^* = R(k<\theta)/(1−k<\theta) = Z<\Phi$
 v. As can be seen in the equation immediately above, the magnitude Z and phase angle are easily derived from the known values of R, k, and θ.
 vi. Converting the polar number into a complex number separates out the real and imaginary components, series resistance and reactance.
 vii. Series Reactance $(Xs) = Z \sin \Phi = 1/wC$, where $w = 2\pi f$
 viii. Series Resistance $(Rs) = Z \cos \Phi$
 ix. Series Capacitance $(Cs) = 1/wXs$
 x. Series Conductance $(Gs) = 1/Rs$
 xi. Rather than a series model, the impedance can also be modeled as a parallel combination of reactance (Xp) and resistance (Rp), as one skilled in the art will understand.
 xii. Parallel Capacitance (Cp) can be calculated from the series reactance and resistance as follows: $C_P = -X_S/[w(R_S^2 + X_S^2)]$
 xiii. Parallel Resistance (Rp) can be calculated as follows: $R_P = -X_S/wC_PR_S$
 xiv. Parallel Reactance (Xp) can be calculated as follows: $X_P = -1/wC$
 xv. Parallel Conductance $(Gp) = 1/Rp$.

In various embodiments of the invention, any time series of data pairs: (Z and Φ), (Rp and Xp), (Gp and Cp), (Xs and Rs) or (Gs and Cs) can be used to represent the resultant cure data (also referred to as "process curves" or equivalently impedance data streams).

In this document, reference to capacitance (C), conductance (G), reactance (X) or resistance (R) is generally made irrespective of the type of model selected (e.g., a series model, or a parallel model as described above). The impedance analysis performed by the present invention is the same regardless of which model is selected for use. That is, generic references to C, G, R, and X apply equally to either parallel or series data.

Figure 7:
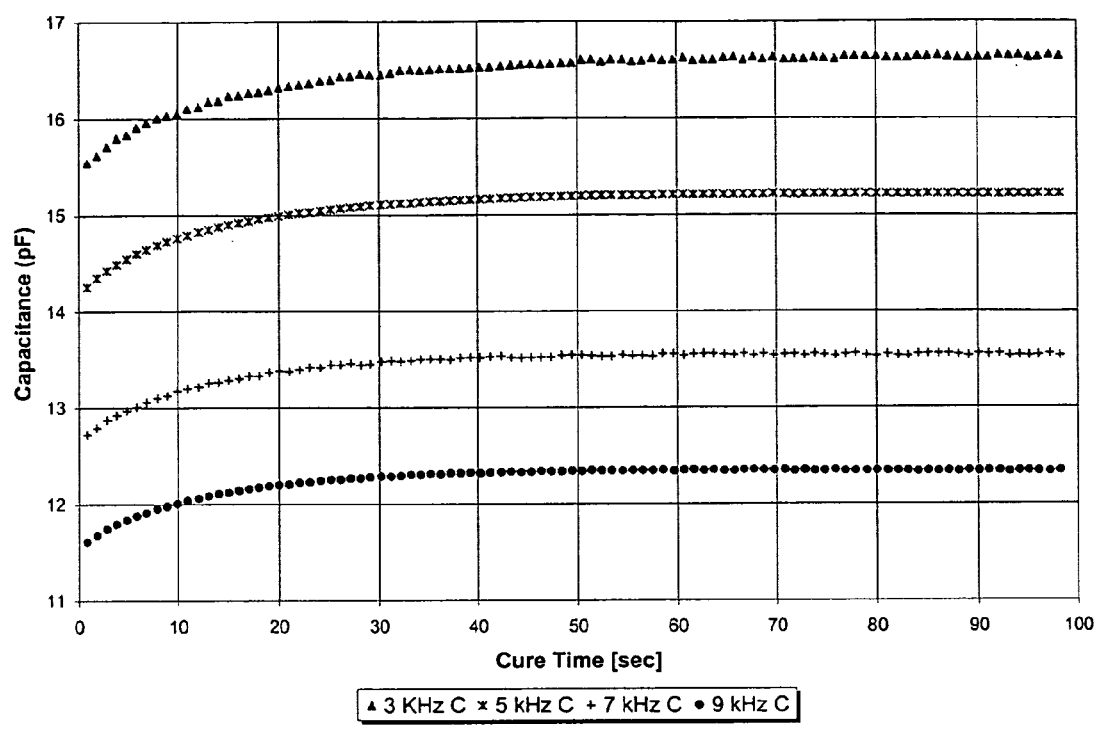
FIG. 7 shows sensor capacitance data collected at 8 frequencies from 3 kHz to 10 kHz.
Figure 8:
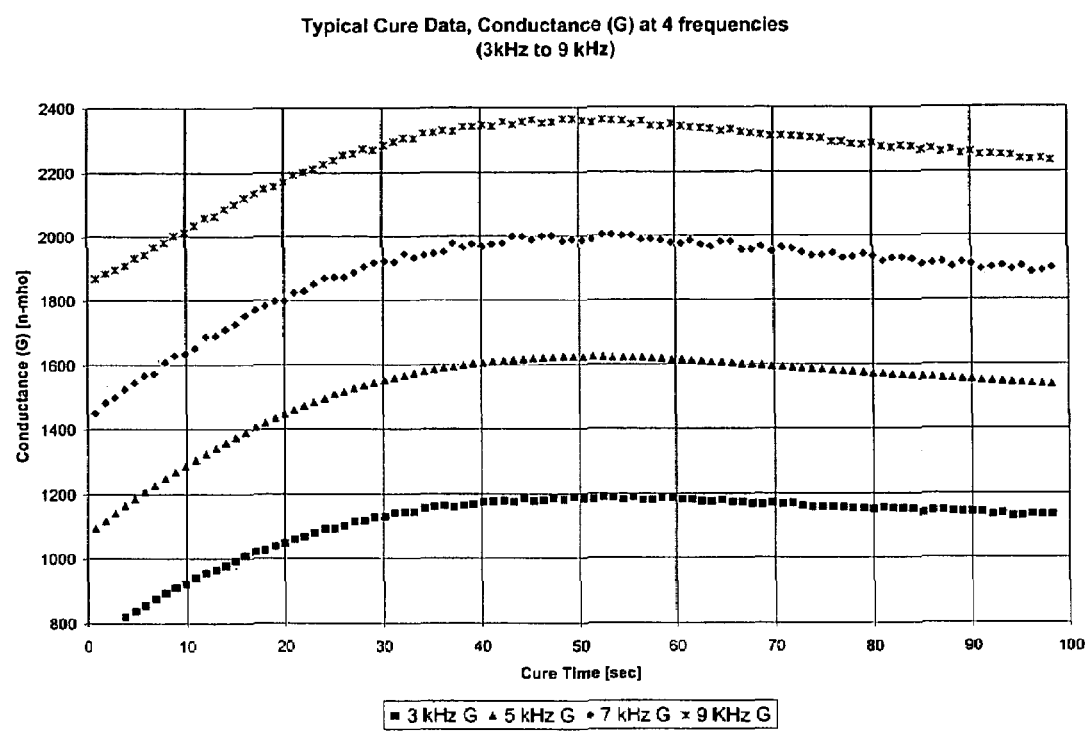
FIG. 8 shows sensor conductance data collected at 8 frequencies from 3 kHz to 10 kHz.

FIG. 7 shows a typical set of capacitance (C) data collected from a rubber compound cure process according to the present invention, wherein the data collected is displayed at 4 different excitation frequencies from 3 kHz to 9 kHz. FIG. 8 shows a typical set of conductance (G) data collected from the same rubber compound cure, wherein the data collected is again displayed for 4 different excitation frequencies from 3 kHz to 9 kHz.

(2.4) Method for Establishing Control Algorithms and/or Formulas

Given that impedance property data, i.e., (Z and Φ), (R and X), and/or (G and C), is capable of being observed and recorded during a rubber compound 16 curing process (e.g., as depicted in FIGS. 7 and 8), the present invention provides a control method for:
 (a) measuring such impedance property data directly in the mass production process of cured rubber compound based parts, and
 (b) reaching a conclusion with respect to proper cure time for a particular production cycle (i.e., the part(s) being currently cured), based on the data measurement from the capacitor 68.

The process for algorithm or formula development is outlined below.

Figure 12:
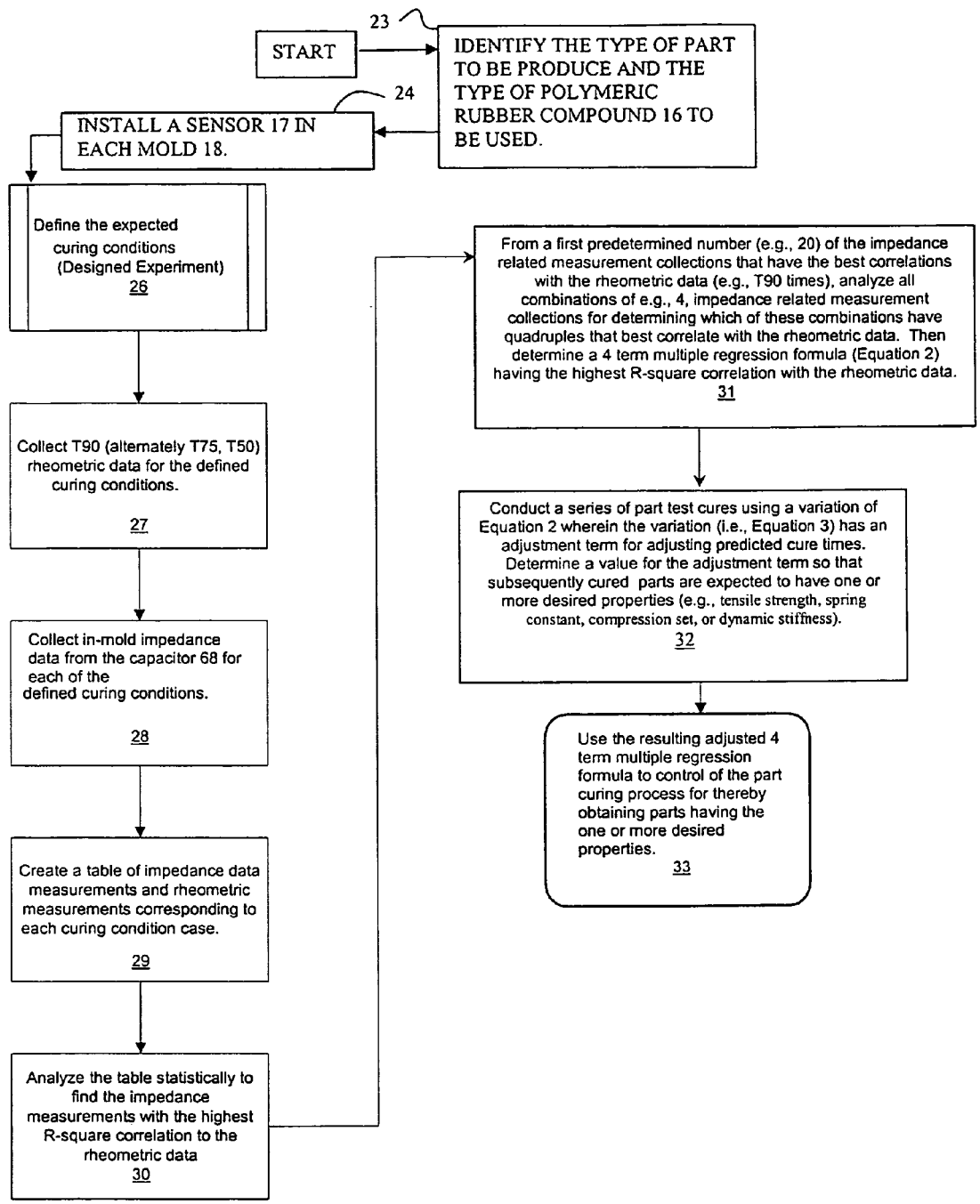
FIG. 12 shows the controller 43 development logic.

(2.4.1) Embodiment for Algorithm Development Using a Production Mold and a Rheometer The following steps of FIG. 12 may be performed when a rheometer is available for use in conjunction with the mold 18:

(Step 23) Identify the application of interest (type of part, type of polymeric rubber compound 16 to be used, and the desired characteristics of the parts to be produced, e.g., compression set, modulus, porosity, solvent swell, differential scanning calorimetry, maximum elongation, enlongation at break, dynamic spring rate, face load, as one skilled in the art will understand).

(Step 24) Install at least one sensor 17 in each production mold 18, so that it can be used to obtain impedance property data on the curing rubber compound 16.

(Step 26) Determine a plurality of curing conditions for producing the desired part, wherein each curing condition identifies one or more important cure parameters and a corresponding value or range for each such parameter. In one embodiment of the invention, curing conditions for two such parameters are determined, e.g., mold temperatures ranges, and rubber compound 16 batch identifiers. Note that the curing conditions may be determined by performing a statistically designed experiment, wherein each curing condition: (i) includes, for at least one parameter that substantially affects the curing process, a corresponding range of variation expected to occur within the normal production curing processes of the rubber compound 16, and (ii) for each such parameter, a particular range of variation that is considered at least possible (if not likely) to occur during the curing of one or more of the rubber compound produced parts.

For example, the variations expected to occur within the normal curing production process includes changes in the composition of the rubber compound 16 being provided to the mold 18. In particular, such rubber compound 16 composition changes typically correspond to changes in the batch of the rubber compound 16 being provided to the molds 18. Thus, unique batch identifiers are used to identify (possibly) different compositions of the rubber compound 16 being used, and which may have different curing characteristics thereby requiring a different a cure time to reach an optimal or desired cure state. Similarly, for mold 18 temperature, the expected variations include, e.g., a +/−5 degree F. change in mold temperature, which could necessitate a different cure time to reach the desired cure state.

Each row of TABLE A following is illustrative of a typical or expected curing condition that may likely occur, wherein the term "nominal" in the mold temperature column of TABLE A refers to a predetermined temperature that is believed to be at least an acceptable curing temperature, and likely a prefened curing temperature. Accordingly, for each table row, by curing one or more rubber compound 16 samples according to the curing condition specified in the row, cure data can be obtained (which may be considered as calibration data in that this data becomes reference data to which various correlations are performed), wherein (as described hereinbelow) a first portion of this cure data includes impedance signal data (e.g., Z, Φ, R, X, G or C values) obtained from the capacitor(s) 68, and a second portion that includes curing related data obtained from samples cured in a rheometer, wherein such curing related data (also refened to as rheometric data) includes one or more curing times for curing a sample to conesponding cure states indicative of, e.g., a particular elasticity, and/or a particular compression set property.

TABLE A

| Case number | Mold temperature | Batch number |
|---|---|---|
| 01 | 5 F. below nominal | Batch A |
| 02 | 5 F. below nominal | Batch B |
| 03 | 5 F. below nominal | Batch C |
| 04 | nominal | Batch A |
| 05 | nominal | Batch B |
| 06 | nominal | Batch C |
| 07 | 5 F. above nominal | Batch A |
| 08 | 5 F. above nominal | Batch B |
| 09 | 5 F. above nominal | Batch C |

(Step 27) Assuming that a plurality of curing conditions have been defined as in TABLE A above, the above-mentioned rheometric data can be collected using a rheometer (not shown) in a more controlled environment than that provided for mass part production using a mold 18. In particular, each of the in-mold curing conditions can be simulated with a corresponding rubber compound 16 sample in a rheometer with the appropriate environmental curing conditions provided, thereby obtaining various types or rheometric data for the curing condition. As will be described further hereinbelow, such rheometric data is used in combination with impedance related data (e.g., obtained from the first portion of the cure data that is, in turn, obtained from the curing of in-mold test samples) to determine cure prediction data, wherein such cure prediction data is for predicting: (i) an in-mold cure time for a desired likely or default cure state, and/or (ii) an in-mold relative rate of cure. In particular, for dominant environmental curing factors such as temperature, a likely or predicted cure time and/or rate of cure can be determined for each of a plurality of mold 18 temperatures, wherein such cure prediction data can be effectively used in predicting a cure time/rate of parts made from various rubber compound batches. For example, it is an aspect of the invention that such cure prediction data can be used not only for providing cure predictions for curing parts made from the rubber compound batches used in obtaining the prediction data, but additionally, the prediction data can be used for providing cure predictions for curing parts made from rubber compound batches not used in obtaining the prediction data.

In one embodiment of the invention, the rheometric data includes, what is known in the art as, the "T90 time" for each rubber compound sample cured in the rheometer, wherein the T90 time is the time that the curing rubber compound 16 reaches 90% of its desired final elastic torque maximum. However, it is within the scope of the invention to provide other cure state times in the rheometric data. For example, as one skilled in the art will understand after reviewing all the steps of FIG. 12, the following cure times may also be used: (a) T50 time for curing the rubber compound 16 to 50% of its desired final elastic torque maximum, (b) T75 time for curing the rubber compound 16 to 75% of its desired final elastic torque maximum, and/or (c) other times related to the rubber compound's desired final elastic torque, or related to tensile strength, spring constant, compression set, or dynamic stiffness.

So for each of the curing conditions (i.e., rows) described in Table A above, a rheometer may be set to the specified temperature, with a sample for the specified rubber compound 16 batch therein, for measuring, e.g., the T90 time. An illustrative example of the type of rheometric data collected by the present invention is as follows (TABLE B):

TABLE B

| Case number | Mold temperature | Batch number | Proper Cure time (T90: seconds) |
|---|---|---|---|
| 01 | 5 F. below nominal | Batch A | 120 |
| 02 | 5 F. below nominal | Batch B | 135 |
| 03 | 5 F. below nominal | Batch C | 142 |
| 04 | nominal | Batch A | 100 |
| 05 | nominal | Batch B | 110 |
| 06 | nominal | Batch C | 115 |
| 07 | 5 F. above nominal | Batch A | 90 |
| 08 | 5 F. above nominal | Batch B | 95 |
| 09 | 5 F. above nominal | Batch C | 98 |

Fundamentally, the purpose for the rheometric data is to establish relative rubber compound 16 cure rates and/or cure times that are likely to occur during, e.g., mass production of cured parts. Since in-mold conditions may vary significantly from rheometric instrument conditions, the optimum production cure time for a given part(s) may not be the same as the T90 time from the rheometer. However, the rheometric data does provide useful information regarding the relative cure rates and times observed due to the variation in both rubber compound 16 batch and cure temperature provided at the rheometer. In particular, for such rheometric data obtained from a sufficiently large number of samples (e.g., from a large number of both batches and curing temperatures), the rheometric data can be used for interpolating and/or extrapolating predictions of in-mold cure times/rates as will be described further hereinbelow.

(Step 28) In this step the effects of various curing conditions are determined by curing samples in the mold 18. In particular, for each of the curing conditions (e.g., the rows of TABLE A), the curing condition is created at the mold 18 for curing a rubber compound sample. Accordingly, impedance signal data is obtained from the curing of each such in-mold sample. Examples of graphs of the impedance signal data that is captured from the in-mold curing of such samples is shown in FIGS. 7 and 8.

Multiple rubber compound samples are preferably cured for each in-mold curing condition, and more particularly, at least three such samples are cured per curing condition. For example, a production mold 18 can be set at a temperature 5 degrees below nominal, and batch A of a rubber compound 16 can be provided to this mold for obtaining impedance signal data during the curing of each of three rubber compound samples to the desired cure state (e.g., desired elasticity). Thus, once all the samples for batch A of the rubber compound 16 have been appropriately cured, the rubber compound 16 may then be changed to, e.g., batch B, and the impedance signal data for a plurality of batch B samples can be recorded. Accordingly, this process can be repeated until all designated rubber compound 16 batches have had samples therefrom cured, and accordingly an aggregate collection of impedance signal data is captured that is representative of the curing process for these batches. Note that although variations between rubber compound 16 batches are not, in general, believed to affect part curing as much as mold temperature, such variations can still impact the curing time and/or rate. However, by capturing impedance signal data as described here, most typical variations between rubber compound batches can be reflected in the aggregate collection. Thus, cure prediction data that is derived (in steps 29 and 30 hereinbelow) using this aggregate collection of impedance signal data that is believed to be predictive of the in-mold curing time and/or rate substantially independently of what rubber compound batch is supplied to the mold 18 with the rubber compound to be cured. That is, it is assumed that for a given type of rubber compound the variations between batches of the given type of rubber compound will not vary substantially from the batches used to determine the rheometric data, e.g., of TABLE B above. In particular, for each of the production parts cured in the mold 18 from a single type of a rubber compound, the actual instance or portion of a batch of this rubber compound is assumed to have each of its constituent ingredients in a range provided by some of the instances of the rubber compound obtained from the batches used to determine the rheometric data, e.g., of TABLE B above.

In one embodiment, at least three such rubber compound samples are cured in the mold 18 from each batch, wherein each of the three is cured at a different mold 18 temperature. In other embodiments, there may be additional samples cured. For example, there may be a plurality of samples cured according to the same curing conditions. In particular, for each rubber compound batch and each mold 18 temperature, there may be a plurality (e.g., 3) samples cured, and the impedance related data therefrom combined to obtain a composite for the impedance signal data resulting from the same signal frequency input to the capacitors 68.

When all such simulations (i.e., sample curings) are complete for each mold 18 (and/or each distinct capacitor 68 in each mold), the impedance data obtained (likely in a distinct data file for each sample) will be associated with its corresponding curing condition as illustrated in Table C following.

TABLE C

| Case number | Mold temperature | Batch number | Proper Cure time (T90: seconds) | Associated impedance files |
|---|---|---|---|---|
| 01 | 5 F. below nominal | Batch A | 120 | 01, 02, 03 |
| 02 | 5 F. below nominal | Batch B | 135 | 04, 05, 06 |
| 03 | 5 F. below nominal | Batch C | 142 | 07, 08, 09 |
| 04 | Nominal | Batch A | 100 | 10, 11, 12 |
| 05 | Nominal | Batch B | 110 | 13, 14, 15 |
| 06 | Nominal | Batch C | 115 | 16, 17, 18 |
| 07 | 5 F. above nominal | Batch A | 90 | 19, 20, 21 |
| 08 | 5 F. above nominal | Batch B | 95 | 22, 23, 24 |
| 09 | 5 F. above nominal | Batch C | 98 | 25, 26, 27 |

Note that for simplicity of the remaining description, it will be assumed that there is a single mold 18 and a single capacitor 68 in the mold unless stated explicitly otherwise. One of ordinary skill in the art will readily understand how to apply the invention to a plurality of molds 18 and/or a plurality of capacitors 68 within a single mold 18. For example, the invention can be applied to each mold 18 as if this mold were the only mold. Moreover, the invention can be applied to each of a plurality of capacitors 68 within a single mold 18 as if each such capacitor were the only capacitor, except that a curing time resolving component or task may be required to resolve cure time discrepancies between the outputs from multiple capacitors within the same mold 18. Note, that one such resolving component can be described as follows: in the event that multiple sensors are used in a mold, lag logic may be applied to ensure that the mold is not opened until the longest predicted cure time of all the sensors has elapsed.

(Step 29) Given that the curing conditions have been simulated in both the rheometer and in the mold 18, the present step creates a table (or more generally, an association) for associating for each curing condition, the impedance signal data collected, the rheometric data, and results from at least two mathematical/statistical evaluators of the impedance signal data. In order to describe these evaluators, it worthwhile to define the following terms:

Impedance data stream: A time series of Z, Φ, R, X, G or C impedance values output by the sensor measurement unit 60 during the curing of a single sample/part, wherein this output is the result of the capacitor 68 receiving signal input at a specific corresponding frequency. Each such series entry has a timestamp associated therewith indicating when the impedance signal data corresponding to the entry was obtained from the sensor measurement unit 60.

Window/segment: (Equivalently referred to as merely as a "window" or a "segment") A portion of an impedance data stream corresponding to a particular time period. That is, the portion of the impedance data stream wherein the impedance values of the portion have timestamps that are within the particular time period for the window/segment. Note that one or more impedance data streams can be divided into a plurality of such windows/segments. In one embodiment, there may be 5 or more such windows/segments. These windows/segments may be determined using software written in LabView (a program development tool), available from National Instruments, Austin, Tex. In particular, for each desired impedance data stream segment, the window/segment start time, stop time, and segment length can be automatically generated using preset values or values specified by the user using this software. For example, if a monitored rubber curing process is approximately 100 seconds in duration, the software may automatically segment the data into 20 second blocks of data, resulting in a series of "windows" that start and stop at 0, 20, 40, 60, and 80 seconds. In this example, the first window may start at 0 seconds and end and 20 seconds. The second window may start at 20 seconds and end at 40 seconds, etc.

Note that a window/segment may be a "fixed segment", having a predetermined start time, stop time, and length. Alternately, some segments may be "variable segments", wherein the time duration of such a segment varies according to, e.g., characteristics of values derived from an impedance data stream. For example, such a variable segment may extend timewise for an additional fixed time length after the impedance data stream travels through a maximum or minimum value of an impedance property (e.g., Z, Φ, R, X, G or C).

In various embodiments of the invention, one or more of the following eight mathematical/statistical evaluators are provided for evaluating each of one or more impedance data streams, and obtaining values which will be referred to hereinbelow as "impedance related measurements".

Evaluator 1: For each segment, the maximum impedance value is determined.

Evaluator 2: For each segment, the time of the maximum impedance value is determined.

Evaluator 3: For each segment, the minimum impedance value is determined.

Evaluator 4: For each segment, the time of the minimum impedance value is determined.

Evaluator 5: For each segment, the integrated area under the graph of the segment impedance values vs. time is determined.

Evaluator 6: For each segment, a linear least-squares best fit is performed on the segment entries, and the slope of the resulting line is determined. (i.e., m, in the equation y=mx+b).

Evaluator 7: For each segment, an exponential best fit is performed on the segment entries, and the damping coefficient is determined (i.e., a, in the equation $y=Ae^{-\alpha x}$).

Evaluator 8: For each segment, an exponential best fit is performed on the segment entries, and the amplitude coefficient is determined. (i.e., A, in the equation $y=Ae^{-\alpha x}$).

Note, however, that other impedance related measurements are also contemplated for use in various embodiment of the present invention, such as times and/or impedance values when one or more graphical points described by various derivatives (e.g., inflection points, etc.) occur, one or more coefficients of a polynomial fit to a segment(s), a centroid (or a coordinate thereof) of an area under a graph of a segment, and/or one or more coefficients of a higher order derivative of a curve fit to a segment(s). Additionally, it is within the scope of the present invention to also include evaluators that are not as easily described geometrically, such as a predicted cure time output by an artificial neural network, or an expert (system) rule based evaluator, or a weighted combination of two or more evaluator outputs.

After obtaining impedance related measurements from the evaluators, a data table (or more generally, an association) is created (as illustratively shown by TABLE D following), wherein each row of the table identifies: (1) a particular curing condition, (2) the conesponding T90 time, and (3) a plurality of the impedance related measurements for various windows and from various evaluators. Note that only a portion of an actual data table is shown in TABLE D. An actual data table may include, e.g., up to or more than 640 impedance related measurements per row, wherein the 640 impedance related measurements can be obtained as follows: (8 signal frequencies input to the sensor circuit 62) times (2 data types (R and X, or G and C, or Z and D)) times (5 windows) times (8 impedance related measurements from the evaluators) 640 measurements. Said another way, TABLE D below may include 640 impedance related measurement collections (i.e., columns) that can be used for determining cure predictors (e.g., cure prediction equations) that, in turn, can be subsequently used to generate cure predictions or estimates of each part of a collection of mass produced parts cured in mold 18. For simplicity of discussion, the term "impedance data column" shall denote the impedance related measurements obtained from a fixed one of the evaluators receiving input from a fixed one of the windows whose impedance measurements, in turn, were obtained for a single frequency of signals input to the sensor circuit 62.

TABLE D

| File number | Mold temperature | Batch identifier | Proper Cure time (T90: seconds) | Window 1, data stream 1, slope | Window 1, data stream 1, max | Window 1, data stream 1, time of max |
| --- | --- | --- | --- | --- | --- | --- |
| 01 | 5 F. below nominal | Batch A | 120 | .117 | 10.13 | 48 |
| 02 | 5 F. below nominal | Batch A | 120 | .114 | 10.21 | 48 |
| 03 | 5 F. below nominal | Batch A | 120 | .112 | 10.24 | 49 |
| 04 | 5 F. below nominal | Batch B | 135 | .105 | 10.25 | 51 |
| 05 | 5 F. below nominal | Batch B | 135 | .105 | 10.13 | 51 |
| 06 | 5 F. below nominal | Batch B | 135 | .108 | 10.18 | 51 |
| 07 | 5 F. below nominal | Batch C | 142 | .099 | 10.33 | 53 |
| 08 | 5 F. above nominal | Batch C | 142 | .098 | 10.09 | 52 |
| 09 | 5 F. above nominal | Batch C | 142 | .101 | 10.20 | 53 |
| 10 | nominal | Batch A | 100 | .156 | 10.33 | 39 |
| Etc. | Etc. | Etc. | Etc. | Etc. | Etc. | Etc. |

(Step 30) Given that there are now a large number of "cached" measurements (i.e., the impedance data streams themselves, and the impedance related measurements obtained for each segment in Step 29(*b*)), a search of the cached measurements is performed to find at least one (and preferably a plurality) of the impedance data columns that appears to most strongly correlate with the rate and/or time of cure of the rubber compound 16 as the curing condition varies. This is done by first finding the impedance data column(s) in the cached measurements with the highest correlation to the rheometric data (e.g., the corresponding T90 data). For example, since each of the impedance data columns is obtained from the curing of the in-mold samples at various environmental curing conditions (e.g., variations in batches, in mold temperatures), each such impedance data column can be correlated with, e.g., corresponding rheometric T90 times for determining one or more of the impedance data columns that best correlates with the variations in T90 times for the same environmental curing conditions.

A simple illustrative example will now be provided to further show how the conelation between the impedance data columns and the T90 times is determined. Assume for each of a plurality of samples of a given rubber compound batch that both of the following data (a) and (b) below are obtained for the curing condition parameter(s) of interest (e.g., curing temperature):

(a) the T90 time, and (b) for a signal input to the sensor circuit 62 (for an in-mold sample) where the signal input has a frequency of, e.g., 200 Hz, and for a segment starting at, e.g., 15 seconds after commencement of the in-mold sample cure and extending for 15 seconds, the following two impedance data columns are obtained: (i) the slope of the best linear fit to the portion of the impedance data stream for the segment 9 (i.e., the output from Evaluator 6 above), and (ii) the integral, over the time period of the segment, for determining of the area under the curve corresponding to a graph of the segment data (i.e., the output from Evaluator 5 above).

Further assume that the following results are obtained in TABLE E.

TABLE E

| Identifier of Impedance Related Data for Segment 15–30 seconds | Batch Identifier | Temperature (F.) | T90 time (minutes) | Best Fit Linear Slope (Evaluator 6) | Area Under the Curve (Evaluator 5) |
|---|---|---|---|---|---|
| 1 | A | 350 | 3.0 | 1.0 | 300 |
| 2 | A | 375 | 2.0 | 1.0 | 200 |
| 3 | A | 400 | 1.0 | 1.0 | 100 |
| 4 | B | 350 | 4.0 | 1.0 | 400 |
| 5 | B | 375 | 3.1 | 0.95 | 310 |
| 6 | B | 400 | 1.1 | 0.97 | 110 |
| 7 | B | 425 | 0.7 | 1.0 | 70 |
| 8 | C | 350 | 3.1 | 1.0 | 310 |
| 9 | C | 375 | 2.2 | 0.98 | 220 |
| 10 | C | 400 | 1.1 | 0.99 | 110 |

As can be readily seen from TABLE E, there is effectively no correlation between T90 times and the best fit linear slopes output by Evaluator 6. However, there is a very good (in fact perfect) correlation between the T90 times and the area under the curve evaluations output by Evaluator 5. Thus, in the present Step 30, of the two Evaluators 5 and 6, Evaluator 5 and its corresponding impedance related measurements would be selected as having the highest correlation with the rheometric data.

Figure 9:
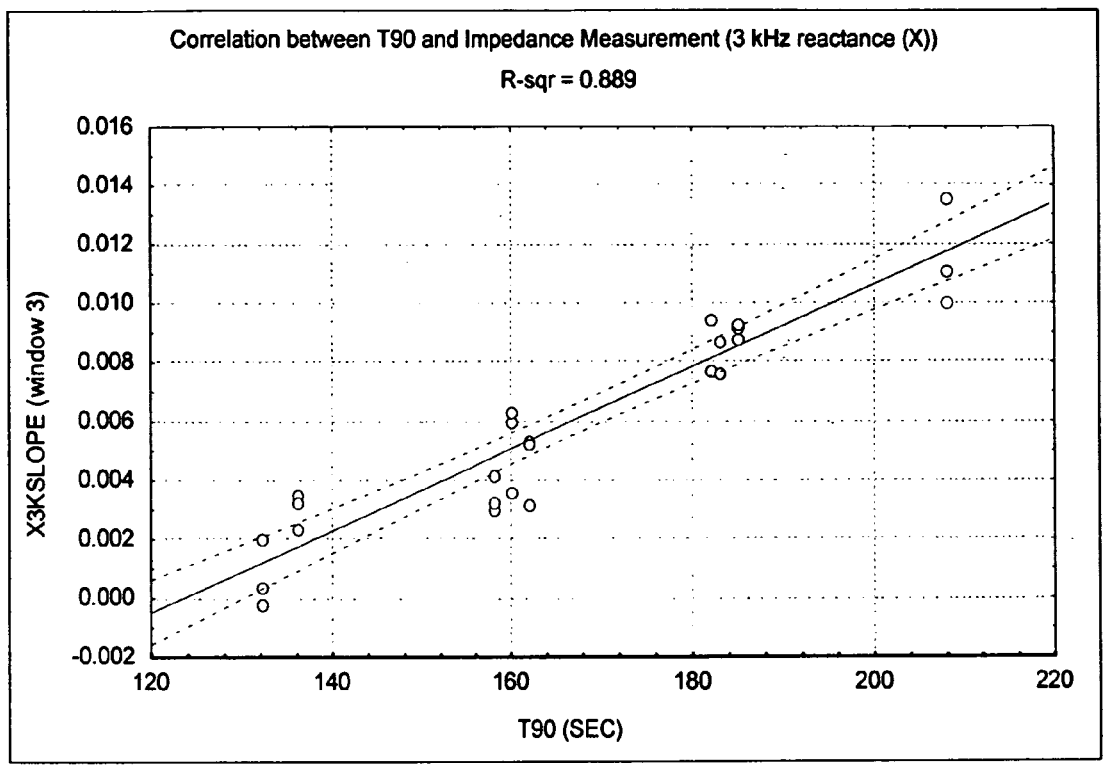
FIG. 9 shows the correlation between observed T90 times and an impedance measurement.

Software, written in LabView may be used to systematically perform such correlations between the T90 data and the impedance data columns output from the various evaluators. Subsequently, once the impedance data columns from the evaluators are determined, the impedance data columns are ranked according to how well they correlate with, e.g., the T90 data. The impedance data column yielding impedance related measurements that are most reflective of the T90 cure time/rate are then identified. FIG. 9 shows a typical correlation between observed T90 times and the impedance data column obtained from the Evaluator 6 for a plurality of curing temperatures (the temperatures are not represented in FIG. 9).

Note that the present invention is not limited to using a single correlation between: the T90 (or other rheometric data), and the impedance data column from just one of the evaluators as will be further described hereinbelow. Moreover, as will also be described further hereinbelow, the above described process of: (1) correlating the impedance data columns from each evaluator with the T90 data, and then (2) selecting one or more of the best correlations can be used to predict in determining an estimated cure time and/or rate for parts that are subsequently cured in the mold 18. For example, assuming a best fit curve (or line) is obtained from correlating an evaluator's output with the corresponding T90 times (such as in FIG. 9), then the line can written in the line equation form:

$$T90 = A^*[\text{evaluator output}] + B \quad \text{(Equation 1),}$$

and for the graph of FIG. 9 this equation becomes:

$$T90 = A^*[X3Kslope] + B \quad \text{(Equation 1A),}$$

wherein A is the slope $\Delta X3Kslope/\Delta T90$, and B is the T90 axis intercept. Therefore, using this best fit line, an estimate of a T90 cure time for each subsequent part cure can be determined. That is, during each subsequent part cured in the mold 18, the term, X3Kslope, can be computed for the particular window in which the above correlation was determined, and then the X3Kslope value is inserted into the line equation (Equation 1A) above (wherein the coefficients A and B have been previously determined). The resultant (T90) time output is an indication of a T90 cure time for the part. Note that this technique of predicting or estimating a cure time/rate does not require measuring or using the temperature of mold 18. However, it is within the scope of the invention that when curing production parts, mold 18 temperature can be also used, e.g., by including the mold temperature measurement in the designed experiment (as described in Step 26 above) and adding the mold temperature in to the cure time equation via multiple regression of the temperature data with the impedance data.

(Step 31) The accuracy of predicting a T90 cure time can be improved through the use of a multiple regression technique. In particular, since there are a variety of evaluators available for outputting impedance related measurements when curing a part, a combination of these measurements can be used to provide a better reflection of the part's cure state than any one of the measurements. For example, instead of estimating a part's curing time/rate from a linear equation of a single evaluator output as in Equation 1A of Step 30, a linear multiple regression using the outputs from a plurality of the evaluators can be performed to estimate a (T90) part curing time. In one embodiment, such a multiple regression is performed by first selecting from the 640 impedance data columns described in Step 29 above (e.g., selecting from the columns of TABLE D), a plurality of the columns that most closely correlate with the T90 times. In particular, an R-square correlation value is first determined for each of 640 impedance data columns, wherein each R-square correlation value determines a similarity between the behavior of a corresponding one of the 640 impedance data columns, and the column of the T90 times. Then a plurality of the 640 impedance data columns having the highest R-square values are identified. In one embodiment of the invention, twenty of the 640 impedance data columns with the highest R-square values are identified. Subsequently, from the identified impedance data columns, all possible combinations of four of these columns are determined, and for each of the combinations, a 4 term multiple regression is performed against the T90 (column) data. In particular, such a multiple regression is performed by correlating the entries of the T90 column with their corresponding quadruple of impedance related measurements for the four impedance data columns of the combination (i.e., each T90 entry corresponds with the quadruple of impedance related measurements that are obtained under the same curing condition). Accordingly, a corresponding multiple regression equation in the following form is obtained:

$$T90 = A_1*Z_1 + A_2*Z_2 + A_3*Z_3 + A_4*Z_4 + B \quad \text{(Equation 2)}$$

where all the $A_k$ terms ($1 \leq k \leq 4$) and the B term are regression determined coefficients, and each of the $Z_k$ terms ($1 \leq k \leq 4$) is determined in the same manner as the impedance related measurements of the $k^{th}$ column of the four impedance data columns identified for performing the multiple regression. That is, each $Z_k$ term is an output from the evaluator used to obtain the impedance related measurements of the $k^{th}$ impedance data column of the four columns when the evaluator's input is provided from the particular signal input frequency to the sensor circuit 62, and the particular curing time window/segment that also corresponds to the $k^{th}$ column. Accordingly, one of these multiple regression equations having the best R-squared correlation with the T90 data is selected for use in predicting T90 cure times of parts curing in the mold 18. Therefore, for controlling the rubber compound part curing process, and in particular, predicting when a curing part will be T90 cured, only the 4 impedance related measurements $Z_k$ need be determined during the part's curing so that the resulting $Z_k$ values can be inserted into the selected Equation 2 in order to calculate the estimated T90 cure time for the part.

Figure 10:
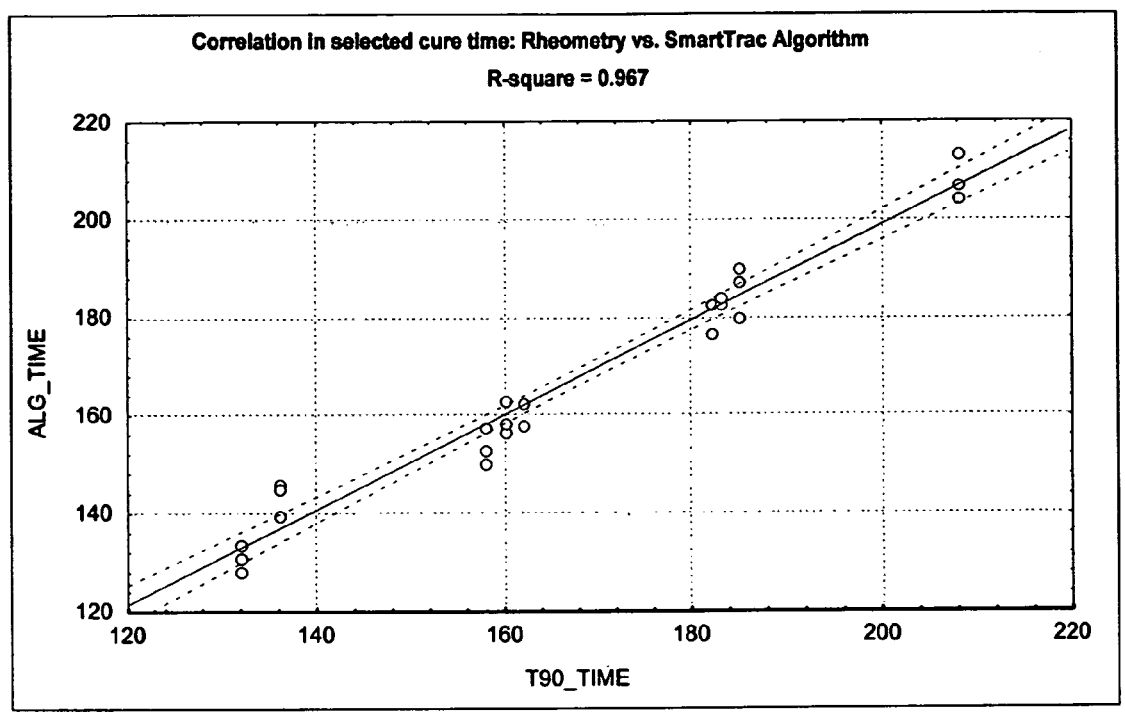
FIG. 10 Shows the correlation between observed T90 times and 4-term multiple regression of impedance measurements.

FIG. 10 shows a plot of the resulting computed cure times versus the corresponding T90 times, using a selected four-term multiple regression instance of Equation 2. Note that there is an improvement in R-square from 0.889 (FIG. 9) to 0.967 (FIG. 10).

It is important to note, however, that the initial selection of impedance data columns (equivalently, the selection of twenty evaluators with their corresponding window domains) is not limited to twenty such columns, or evaluators with input domains. In particular, the number of initially selected impedance data columns may be determined by an R-square threshold, wherein columns above the threshold are selected. Accordingly, only one impedance data column may be selected, or a number of such columns larger than twenty. Similarly, the present invention is not limited to a four term multiple regression for obtaining a resulting, more accurate, curing time equation. Indeed, depending on the number of initially selected impedance data columns, the number of terms in such a multiple regression range from two terms up to, e.g., eight or more terms. Moreover, the present invention is not limited to only correlating multiple regressions having a fixed number of terms (e.g., 4 terms as in Equation 2); instead, multiple regressions of varying numbers of terms are also within the scope of the invention.

(Step 32) The cure control Equation 2 selected in Step 31 is responsive to changes in the curing process that effect the cure rate. However, the selected Equation 2 does not necessarily provide a curing time prediction for a specific cure state desired. For example, if the parts are to be cured to a specific elastic torque, the selected Equation 2 may not be able to provide an appropriate cure time prediction. This is due to the fact that the rheometric T90 times used in the correlation are only relative and may not be indicative of the specific properties desired in the production-molded parts.

In order to adjust the cure time output of Equation 2 to provide a more precise production cure time, an adjustment may be used to modify Equation 2 thereby providing a modified version of Equation 2 that computes an "adjusted cure time" that is more accurate in predicting cure times for parts having the desired cure characteristic. In one embodiment, the adjustment can be some multiplicative factor of its original Equation 2 output. That is, the adjustment can be a "modifier" factored into the cure control equation as follows:

$$\text{Predicted Cure Time} = (\text{modifier})*(A1*Z1 + A2*Z2 + A3*Z3 + A4*Z4 + B) \quad \text{(Equation 3)}$$

Figure 11:
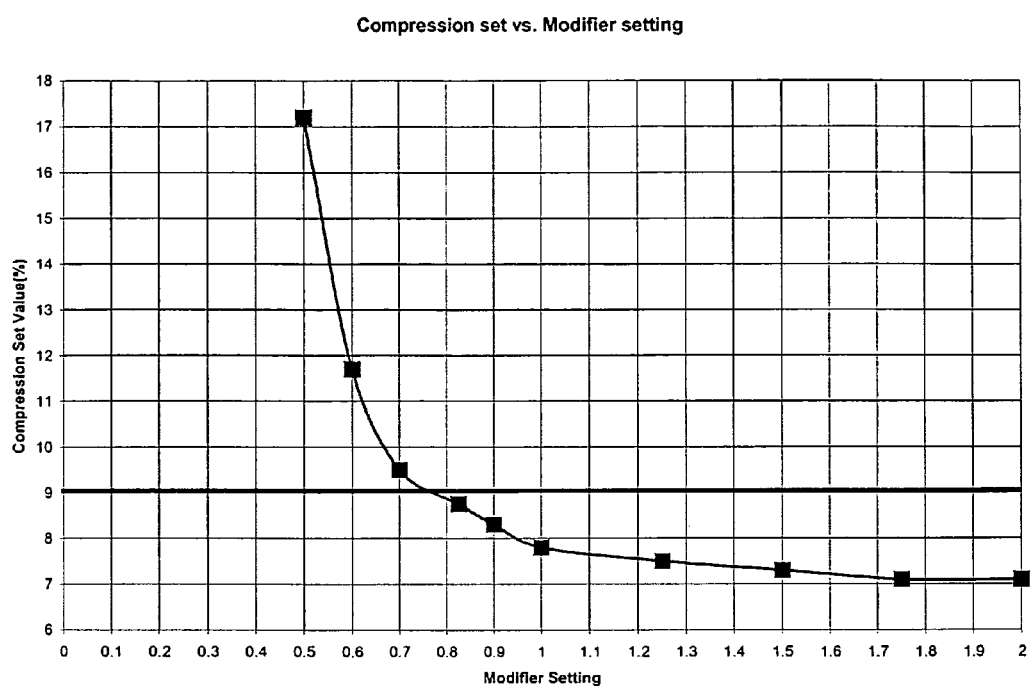
FIG. 11 shows a plot of modifier setting versus a specific part property (compression set).

In order to determine an appropriate (and preferably, an optimum) value for the modifier term of Equation 3, the production curing process is run with the control system 39 (FIG. 13) controlling the cure time for the in-mold rubber compound 16, wherein the control system uses Equation 3 with various settings for modifier term. In particular, for each value (V) of a plurality of values for the "modifier" term, at least one rubber compound 16 test part is cured in the mold 18 to the predicted cure time obtained from Equation 3 with V fixed as the value of the "modifier" term. During the curing of these test parts, the control system 39 changes the "modifier" term's value over a relatively large range (e.g., 0.25 to 2.0), in increments of, e.g., 0.1. Once each test part is cured, measurements of the desired property of the part is determined (e.g., tensile strength, spring constant, compression set, or dynamic stiffness, etc). For the desired property, a plot or graph is generated of the measurements of the desired part property versus. the "modifier" term's various settings. Note that multiple test parts should preferably be cured for each "modifier" value to get a better representation of how each "modifier" value affects the desired part property. An example plot is shown in FIG. 11, wherein a compression set value of 9% or less is the desired property for each of the subsequently to be produced parts. Accordingly, from viewing this graph it is clear that setting the "modifier" term to at least 0.8 would be required, and to include some safety factor, 0.9 may be more appropriate. Any higher modifier setting will simply extend part cure times without improving the compression set property of the parts. Any lower modifier setting will not provide the specified compression set value.

If there are two or more desired properties for the parts, then the above procedure of this step can be followed for each such property. Accordingly, two or more corresponding ranges for the "modifier" term will be obtained. Assuming these ranges overlap, a value from the intersection of these ranges can be used as the value of the "modifier" term in Equation 3.

Note, however, that alternative techniques for "adjusting" a cure prediction equation are within the scope of the invention. In particular, additive terms can be introduced into the right-hand side of Equation 3, wherein such a term(s) could mitigate cure rate time offset.

(Step 33) After choosing an appropriate value for the "modifier" term in Equation 3, the controller 43 (FIG. 13) is ready to be used to control the rubber compound 16 curing process for mass producing parts with the desired property. It should be further understood that development of the cure control algorithm (including setting the modifier) is intended as a one-time event, to be performed only upon initial installation of the part producing equipment. After the algorithm is developed, the system then measures dielectric data with each cure cycle, and then predicts the proper cure time for each cycle.

(2.5) Real-Time Curing Control System and Method

Figure 13:
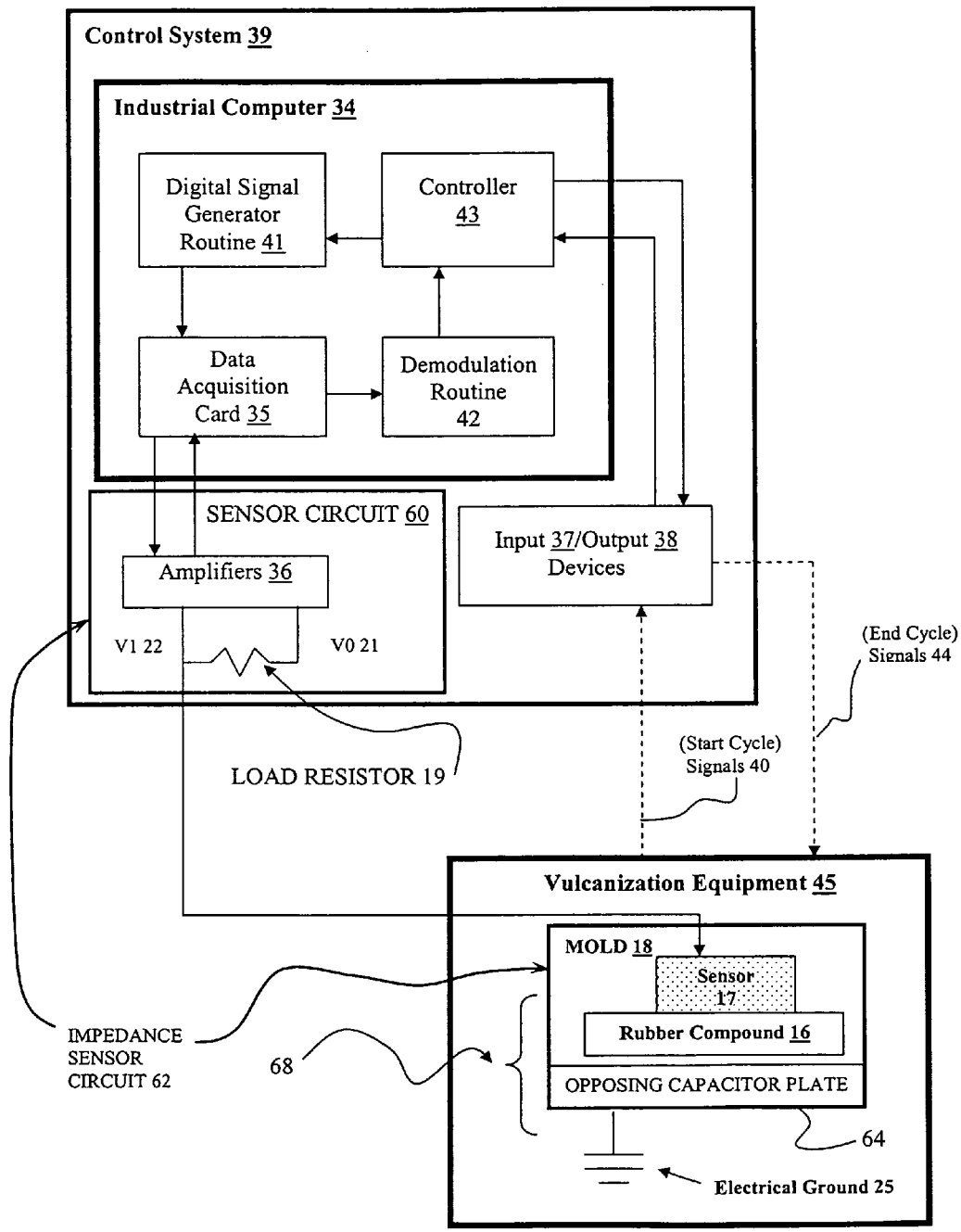
FIG. 13 shows a block diagram of the control system 39.

The control system 39 and its relationship to the vulcanization equipment 45 is shown in FIG. 13. The control system 39 includes:

(1) An industrial computer 34, for processing data as described above.
(2) A controller 43 for controlling in-mold part curing, e.g., by computing curing times according to the version of Equation 3 determined in Step 33 hereinabove.
(3) A data acquisition card 35, installed in the computer 34, for
    i. generating sinusoidal excitation voltages for inputting to the sensor circuit 62, and
    ii. reading and digitizing amplifier 36 outputs.
(4) A digital signal generator software routine 41 for determining and outputting the signal characteristics for a plurality of digital signals.
(5) A digital signal demodulation software routine 42 for demodulating signals received from the sensor 17 and the amplifier(s) 36.
(6) Amplifier(s) 36 for collection of real-time impedance data corresponding to the impedance of the capacitor 68.
(7) Digital input device(s) 37 for receiving (via signals 40) indications of when a curing cycle has started, or rubber compound injected. Examples of such device(s) 37 are any standard or conventional relay.
(8) Digital output device(s) 38 for notifying (via signals 44) operators of an end-of-curing cycle, or energizing relays that open the mold 18. Examples of such device(s) 38 are any standard relay.
(9) An equipment enclosure 5 (FIG. 1) to protect and isolate the components of the present invention.

Figure 14:
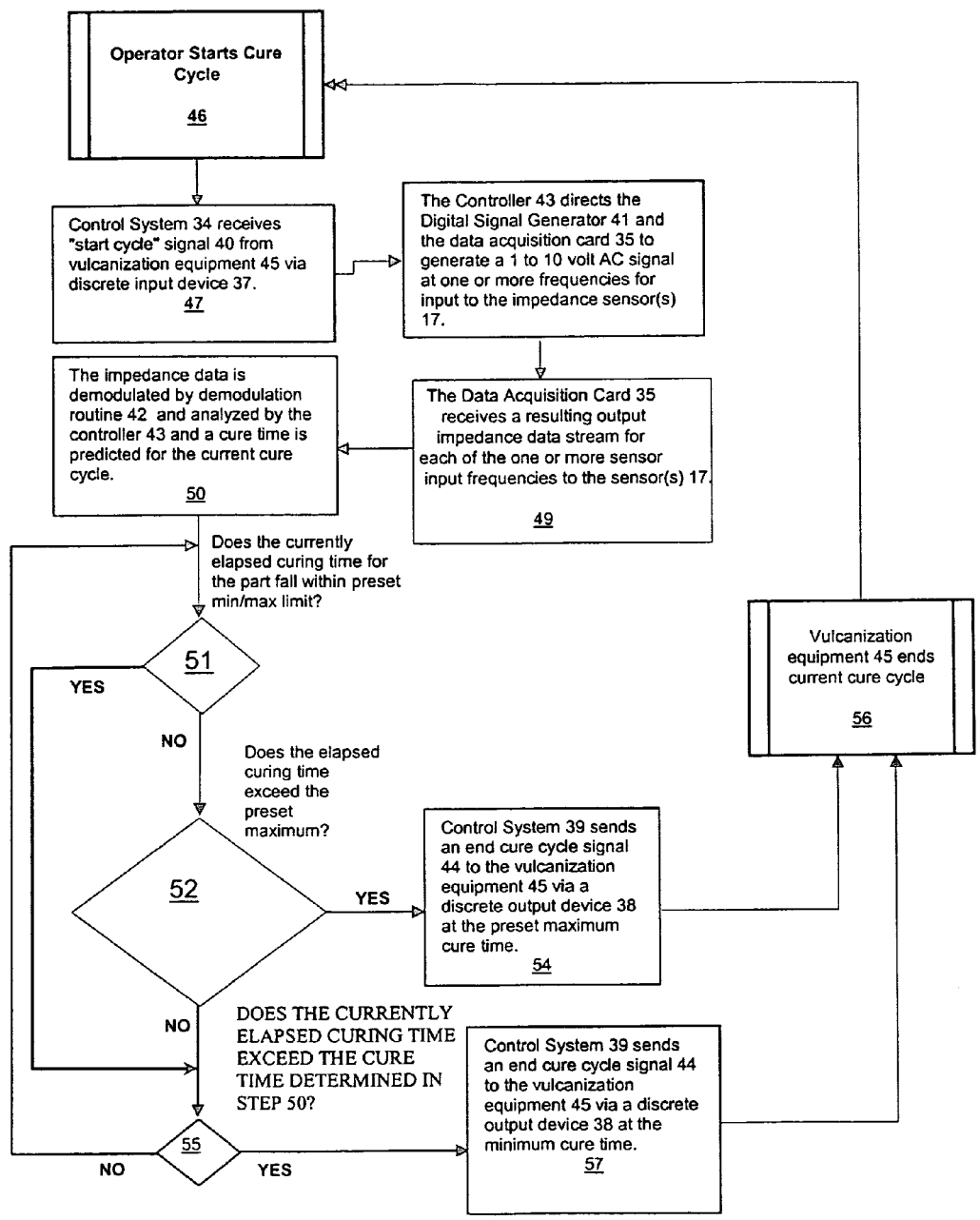
FIG. 14 shows the control system 39 logic.

The actual control of the vulcanization equipment 45 is a relatively straight-forward process as shown in the flowchart of FIG. 14. The process can be summarized as follows:

Steps 46 and 47: When a curing equipment operator starts a new curing production cycle (step 46), a digital input device 37 (FIG. 13) is energized by input signal 40 from the vulcanization equipment 45, and the input device 37 transmits a corresponding signal to the controller 43 that the new curing cycle has started (step 47).

Step 48: The controller 43 directs the digital signal generator 41 and the data acquisition card 35 to generate a 1 to 10 volt AC signal at one or more (preferably a plurality of) frequencies for input to the impedance sensor(s) 17. Accordingly, the digital signal generator routine 41 and the data acquisition card 35 are activated by the controller 43 for generating digital sinusoidal excitations for inputting to one or more capacitors 68 at the one or more frequencies.

Step 49: The data acquisition card 35 and the demodulation routine 42 then receive the responses indicative of impedance characteristics of the capacitor(s) 68. More particularly, the data acquisition card 35 receives the resulting impedance data streams for each of the sensor 17 input frequencies.

Step 50: The impedance data streams are demodulated by the demodulation routine 42 and analyzed by the controller 43 thereby determining a predicted cure time for the current cure cycle (i.e., the part being currently cured in the mold 18). Note that the demodulated sensor responses are recorded by the computer 34 in pairs of impedance data (e.g., Z and Φ, R and X, or G and C). The pairs of impedance data are then segmented (into the segments/windows described hereinabove). Subsequently, the impedance related measurements for the segments/windows are determined by the controller 43 as described hereinabove. Following this, the selected evaluator(s) whose outputs are used in the instance of Equation 3, that has been determined for the particular mold 18 and the desired cured compound characteristics to be obtained, are activated with input from the appropriate window/segment(s). The values for the parameters of the instance of Equation 3 are then provided by the selected evaluator(s) and the controller 43 computes a predicted cure time, from the instance of Equation 3, for the part in mold 18. Step 51: Minimum and maximum cure times may be entered by an operator. The present step uses any such operator predetermined (i.e., preset) minimum and maximum cure times to determine whether or not the currently elapsed curing time for the part falls within this minimum and maximum time range[DJD2].

Steps 52, 54, and 56: If the currently elapsed curing time is greater than (any) operator set maximum curing time, then the controller 43 causes one of the digital output devices 38 to provide an output signal 44 for immediately opening the vulcanization equipment 45. Subsequently, the vulcanization equipment 45 opens.

Steps 55, 57, and 56: If the currently elapsed curing time is within the preset minimum and maximum time limits (from Step 51), or if the currently elapsed curing time is less than the minimum preset curing time limit (from Step 52), then (in Step 55) a determination is made as to whether the currently elapsed curing time has exceeded the predicted cure time computed in step 50. If so the control system 39 sends an end cure cycle signal 44 to the vulcanization equipment 45 via a discrete output device 38 at the minimum preset cure time (Step 57), and the vulcanization equipment 45 opens thereby ending the curing of the current part (Step 56). Alternatively, if the computed cure time is not exceeded, then step 51 and subsequent steps are again performed.

Accordingly, an operator can produce parts using the steps of FIG. 14 together with existing vulcanization equipment 45 which, may include injection molding machines, compression and transfer molding presses, belt presses, autoclaves and the like.

EXAMPLE

Natural Rubber Cure Process

Figure 15:
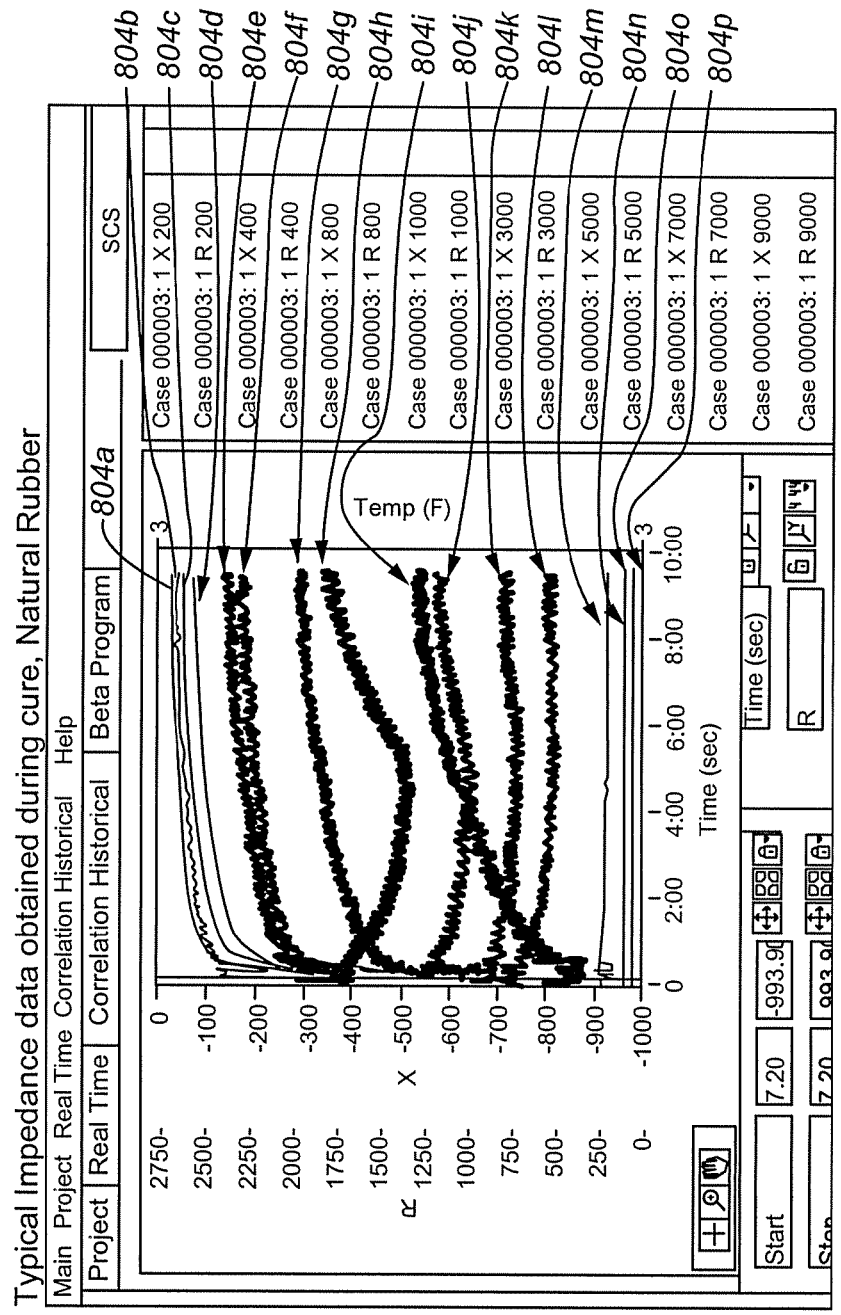
FIG. 15 shows plots of typical impedance data obtained by the present invention during the curing of a sample of natural rubber.

FIG. 15 shows a plot of typical impedance data streams obtained during a cure of natural rubber. Two types of time dependent data are obtained. The types of data are plotted in this figure as: (1) reactance data plots (having vertical axis measurements identified by the "X" column immediately to the left of the plots shown), and (2) resistance data plots (having mega-ohm values for the vertical axis, these values are identified by the column between the "X" and the sideways "R").

For a single rubber sample being cured according to the present invention, eight separate oscillation frequencies are input to the capacitor 68 (having the rubber sample as the rubber compound 16), and resulting reactance and resistance values are obtained for each such oscillation frequency. In particular, the oscillation frequencies may be multiplexed into the capacitor 68 having the curing rubber compound 16 at a sufficiently fast rate so that the cure state does not substantially change during a cycle of inputting all eight oscillation frequencies into the capacitor 68. Accordingly, 16 separate impedance data streams can be collected for each such curing sample. FIG. 15 shows the plots 804a through 804p for 16 separate impedance data streams obtained from a single sample of a natural rubber being cured, wherein the corresponding eight input oscillation frequencies are: 200 Hz, 400 Hz, 800 Hz, 1 kHz, 3 kHz, 5 kHz, 7 kHz, and 9 kHz. It is important to note, however, that a greater or lesser number of oscillation frequencies may be used in various embodiments of the invention (and with various rubber compounds 16); e.g., 4 to 16 different frequencies may used by the present invention. Moreover, the range of the oscillation frequencies may extend from a low frequency of 10 hz to a high frequency of 5 Mhz.

In addition to obtaining the impedance data streams of FIG. 15, a two-factor, three-level designed experiment was established that created a range of curing conditions by varying the mold 18 temperature and accelerator loading in various samples of the natural rubber compound 16 to be cured. The purpose of the experiment was to determine how the collected impedance data streams responded to cure rate changes according to temperature and variations in the natural rubber compound 16. FIG. 16 shows a table of the various curing conditions (i.e., temperature and accelerator loading) examined together with the corresponding resulting T90 times, wherein three replicates were measured in each curing condition. For each condition, rheometry data was obtained as a reference for the expected change in cure rates. The T90 time for each condition is also listed in FIG. 16.

The designed experiment was conducted and an algorithm (i.e., an instance of Equation 3 hereinabove determined as a result of using the Evaluators 1 through 8) was created that showed the correlation between algorithm-predicted cure times and rheometrically-determined T90 times. The algorithm uses various impedance related measurements to approximate the proper cure time.

FIG. 17 illustrates the correlation between measured T90 times and predicted cure times (predicted in-mold by the instance of Equation 3) on the 27 cured natural rubber parts. A very high correlation (r-square=0.99) was observed.

Data observed in this portion of the testing showed very clearly that the method and system of the present invention was sensitive to changes in the curing process both from natural rubber compound variation and mold temperature variation, since the correlation to T90 is so high under all the various curing conditions.

This result demonstrates excellent correlation between impedance measurement and cure rate within the 3 controlled batches (each batch having one of the three levels of accelerator loading).

To further demonstrate usefulness of the present invention in a production environment, a high degree of correlation can be observed through a much wider variety of conditions. That is, seven batches were then tested under a variety of different temperatures (19 different mold conditions) to observe the correlation between rheometry and the in-mold impedance data. FIG. 18 below is a table that describes the various curing conditions examined, including T90 times observed when these conditions were set in the rheometer.

The impedance data streams were collected for each of the nineteen curing conditions (i.e., rows) shown in FIG. 18, wherein impedance data streams from three replicates for each curing condition was collected by monitoring a total of 57 cure cycles. Subsequently, an instance of Equation 3 (described hereinabove) was created.

Figure 19:
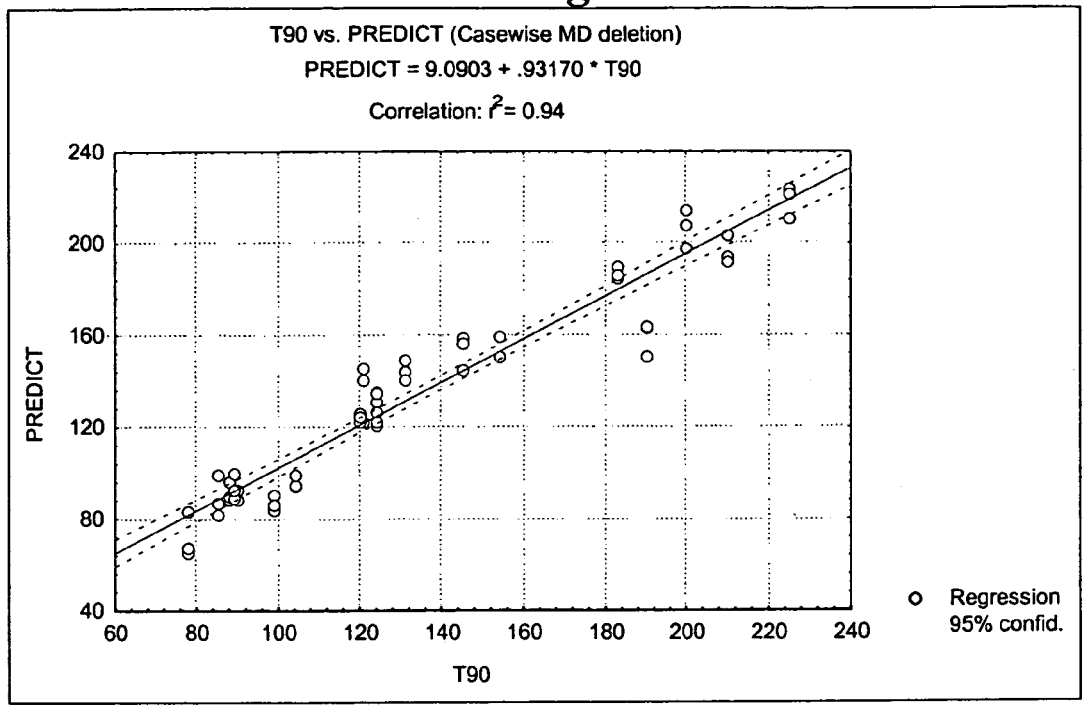
FIG. 19 shows the correlation between the algorithm and rheometry within the broad sampling of natural rubber batches.

FIG. 19 illustrates the correlation between measured T90 times for each given curing condition and the corresponding predicted cure times on the 57 monitored press cycles. A very high correlation (r-square=0.94) was observed. Thus, FIG. 19 demonstrates that the impedance data streams include an informational content that provides an effective rate of cure in the mold 18 over a wide variety of batches, temperatures, and conditions. It should also be noted that all impedance data was taken from actual production runs with production operators.

Prevention of porosity is a critical element in rubber part production, due to the fact that porosity in the finished (e.g., cured) part will drastically reduce the durability and service life of the part.

For the portion of the study described below, the control algorithm, (described above for the curing of natural rubber), was used to control the cure time for a plurality of natural rubber parts. An embodiment of the control system 39 measured the impedance data (i.e., the various resulting impedance data streams), calculated the predicted cure time, and opened the vulcanization equipment 45 when the predicted cure time according to the steps of FIG. 14.

The following results were observed:
(1) present invention can alter the cure time in a rational manner for various in-mold curing conditions; and
(2) the present invention is able to produce parts without porosity, but while still maintaining rapid cure times, faster than would be possible without the present invention.

Fifty-seven cure cycles were run under algorithm control through four different batches of rubber compound 16, and three different temperature settings. Rational changes in cure time control for each curing condition resulted, and no porosity was detected in any of the fifty-seven cures controlled by the embodiment of the invention. FIG. 20 is a table describing for each monitored curing condition, the control algorithm-predicted cure time (i.e., predicted by an instance of Equation 3), and the number of cures performed in each condition. Cure times selected by the control algorithm were rational in that for faster curing batches (as determined from rheometric data), these batches were consistently provided with faster curing predictions under all temperature conditions, and for slower curing batches, these batches were consistently provided with slower curing predictions. Additionally, for rubber samples cured at hotter temperatures, the present invention provided consistently faster predicted curing times as compared to colder temperatures, through all batches. Moreover, no porosity occurred in any of the parts produced. This test demonstrates the capability of the present invention to cure parts at reduced cure times while still avoiding porosity over a wide range of in-mold conditions.

In summary, the present invention insures the production of polymeric rubber compound parts of uniform high quality, in spite of batch-to-batch and in-batch variations in the compound, and variations due to equipment, curing environment, and operator influence. Curing process cycles can be significantly reduced, yields increased, and excellent quality control can be obtained for each cure cycle.

While various embodiments of the present invention have been described in detail, it is apparent that modifications and adaptations of those embodiments will occur to those skilled in the art. It is to be expressly understood, however, that modifications and adaptations are within the scope of the present invention, as set forth in the following claims.

What is claimed is:

1. A method for curing one or more parts, comprising:
   determining, for each evaluator of a plurality of evaluators, a corresponding curing predictive effectiveness;
   wherein the step of determining includes obtaining a plurality of predetermined curing conditions, and curing at least one part at each of the predetermined curing conditions for obtaining an output from each evaluator for each predetermined curing condition:
   wherein for each evaluator, E, of said evaluators, said step of determining determines the corresponding predictive effectiveness according to a correlation between (a1) and (a2) following:
   (a1) outputs by the evaluator E, wherein for each curing condition, $CC_j$, of the curing conditions, there is a portion of the outputs obtained when the evaluator E is provided with a sequence of impedance responses from a device, the sequence of impedance responses being indicative of impedance measurements of the at least one part being cured at its the curing condition $CC_j$, and in curing equipment that is also to be used in curing a subsequent part, and
   (a2) for each curing condition, $CC_k$, of the curing conditions, a curing time obtained from curing a curable compound at the curing condition $CC_k$, wherein the curable compound is expected to have a composition corresponding to the at least one part cured at the curing condition $CC_k$;
   providing, for each of a plurality of predetermined frequencies, an electrical current to the device, wherein the device outputs signals indicative of impedance measurements for curing the subsequent part in the curing equipment;
   receiving, for each of said frequencies, an impedance data stream including a sequence of impedance responses from said device during the curing of the subsequent part;
   for each of one or more of the evaluators, activating the evaluator for obtaining a corresponding result related to a prediction of a cure time of the subsequent part, when the evaluator is provided with a corresponding activation input from one of said impedance data streams;
   using the corresponding results from the one or more evaluators for obtaining a predicted cure time for the subsequent part;
   wherein a step of identifying is performed prior to said step of using, and said step of identifying identifies at least one of the evaluators, $E_1$, for predicting a cure time for the subsequent part, wherein the corresponding predictive effectiveness for $E_1$ is better than the corresponding predictive effectiveness of at least one other of the evaluators.

2. The method of claim 1, wherein each of the curing conditions includes at least a curing temperature, and an identifier for identifying a particular batch from which a rubber compound is obtained as the curable compound.

3. The method of claim 1, wherein for each of the one or more evaluators, the corresponding activation input includes a predetermined segment of an entire impedance data stream indicative of the impedance measurements of a curable compound in response to a particular one of the frequencies being input to the device.

4. The method of claim 3, wherein said particular frequency is one of the predetermined frequencies.

5. The method of claim 1, wherein the rubber compound includes a rubber polymeric compound.

6. The method of claim 1, wherein said curing equipment includes at least one of: an injection molding equipment, a compression molding equipment, a transfer molding equipment, a belt press, and an autoclave.

7. The method of claim 1, wherein the curable compound includes at least one of: styrene-butadiene, polybutadiene, polyisoprene, ethylene-propylene, butyl, halobutyl, nitrile, polyacrylic, neoprene, hypalon, silicone, fluorocarbon elastomers, polyurethane elastomers, natural rubber and hydrogenated nitrile-butadiene rubber.

8. The method of claim 1, wherein for each curing condition, CC, of at least most of the curing conditions, a curable compound from which the at least one part is curing at the curing condition CC, and the curable compound of (a2) for at CC are from a same curable compound batch.

9. The method of claim 1, wherein a curable compound cured for creating the subsequent part has each of its constituent ingredients in a range of some instance of the curable compound that is cured to create the at least one part at one of the curing conditions.

10. The method of claim 1, wherein for each curing condition, the curing time is indicative of an elapsed time for curing a corresponding curable compound to a predetermined elastic torque value.

11. The method of claim 10, wherein each curing time is indicative of an elapsed time for curing the corresponding curable compound to a percentage of a maximum elastic torque.

12. The method of claim 1, wherein said determining step includes performing a statistical correlation between the outputs of (a1), and the curing times of (a2).

13. The method of claim 1, wherein the curing times of (a2) are determined using a rheometer.

14. The method of claim 1, wherein at least one of the evaluators determines one of: (1) a maximum impedance value, (2) a time value for a maximum impedance, (3) a time value for a minimum impedance, (4) a value indicative of an area under a graph of a series of impedance values, (5) a slope obtained from a series of impedance values, (6) a dampening coefficient of a curve fitted to a series of impedance values, and (7) an amplitude coefficient of a curve fitted to a series of impedance values.

15. The method of claim 14, wherein at least most of (1) through (7) are determined by the evaluators.

16. The method of claim 1, wherein at least a majority of the plurality of predetermined frequencies are in a range of 10 hz to 5 Mhz.

17. The method of claim 1, wherein the number of different frequencies of the plurality of predetermined frequencies can be greater than or equal to 4.

18. The method of claim 1, wherein said device includes at least one of: a non-bridged dielectric or impedance measurement circuit, and a voltage divider circuit for determining the impedance responses of (a1).

19. The method of claim 18, wherein said device determines the impedance responses of (a1) using an output from the non-bridged dielectric or impedance measurement circuit.

20. The method of claim 18, wherein said device determines the impedance responses of (a1) using an output from the voltage divider circuit.

21. The method of claim 1, wherein an electrode is operatively connected to the curing equipment and the device, wherein the impedance measurements for the subsequent part, and the impedance responses for the subsequent part are indicative of responses from a capacitor formed using the electrode and a curable compound from which the subsequent part is created.

22. The method of claim 1, further including a step of dividing at least one of the impedance data streams into a plurality of segments.

23. The method of claim 22, wherein for at least one of the evaluators, its corresponding activation input is one of the segments.

24. The method of claim 1, wherein said step of using includes combining the corresponding results from at least two evaluators.

25. The method of claim 24, wherein said combining step includes providing the corresponding results from the at least two evaluators to a predetermined multiple regression equation.

26. The method of claim 1, further including the step of:
selecting the outputs of (a1) for each of a subset of the evaluators and their corresponding activation inputs;
combining the selected outputs in each of a plurality of combinations; and
determining at least one of the combinations having a predictive effectiveness that is better than the predictive effectiveness of at least one of the evaluators.

27. The method of claim 26, wherein said selecting step includes choosing for the outputs of (a1) that correlate better with the curing times of (a2) than the outputs of (a1) that are not chosen.

28. The method of claim 26, wherein said combining step includes:
obtaining a value indicative of a maximum number of the outputs to be provided in each of the combinations.

29. The method of claim 26, wherein said step of determining at least one of the combinations includes performing a multiple regression of at least some of the combinations against the curing times of (a2).

30. A method for curing one or more parts, comprising:
obtaining, for each of a plurality predetermined curing conditions, a corresponding curing time for curing a corresponding curable material;
determining, for each evaluator of a plurality of evaluators, a corresponding curing predictive effectiveness;
wherein the step of determining includes, for each of the predetermined curing conditions, curing at least one part at the predetermined curing condition for obtaining an evaluator output from each evaluator when the evaluator is provided with data indicative of corresponding impedance responses from the curing of the part at the predetermined curing condition;
wherein for each evaluator, E, of said evaluators, said step of determining determines the corresponding predictive effectiveness according to a correspondence between (a1) and (a2) following:
(a1) the evaluator outputs by the evaluator E, and
(a2) the curing times;
prefening one or more of the evaluators over another of the evaluators using their respective corresponding curing predictive effectiveness;
for each of the preferred one or more evaluators, activating the evaluator for obtaining a result related to a prediction of a cure time of a subsequent part, when the evaluator is provided with data indicative of corresponding impedance responses from the curing of the subsequent part;
wherein a step of identifying is performed prior to said step of using, and said step of identifying identifies at least one of the evaluators ($E_1$) for predicting a cure time for the part, wherein the predictive effectiveness for $E_1$ is better than the predictive effectiveness of at least one other of the evaluators.

31. The method of claim 30, wherein the step of prefening includes determining a corresponding weighting for each of the one or more evaluators.

* * * * *